US012690867B2

(12) United States Patent　(10) Patent No.: US 12,690,867 B2
Weir et al.　(45) Date of Patent: Jul. 28, 2026

(54) SYSTEM AND METHOD FOR VARIABLE VELOCITY INSTRUMENT

(71) Applicant: INTUITIVE SURGICAL OPERATIONS, INC., Sunnyvale, CA (US)

(72) Inventors: David W. Weir, San Carlos, CA (US); Gabriel F. Brisson, Livermore, CA (US); William A. Burbank, Sandy Hook, CT (US); Amir Chaghajerdi, Los Altos, CA (US); Patrick Flanagan, San Diego, CA (US); Pushkar Hingwe, Los Altos, CA (US); Andrew Wilson, Glastonbury, CT (US); Donald F. Wilson, Jr., Santa Clara, CA (US); Matthew A. Wixey, Trumbull, CT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 16 days.

(21) Appl. No.: 18/662,686

(22) Filed: May 13, 2024

(65) Prior Publication Data

US 2024/0293121 A1　Sep. 5, 2024

Related U.S. Application Data

(63) Continuation of application No. 17/160,288, filed on Jan. 27, 2021, now Pat. No. 12,053,179, which is a
(Continued)

(51) Int. Cl.
*A61B 17/00* (2006.01)
*A61B 17/068* (2006.01)
(Continued)

(52) U.S. Cl.
CPC .. *A61B 17/07207* (2013.01); *A61B 17/00234* (2013.01); *A61B 34/00* (2016.02);
(Continued)

(58) Field of Classification Search
CPC ............ A61B 17/00234; A61B 17/068; A61B 17/07207; A61B 17/0727
See application file for complete search history.

(56) References Cited

U.S. PATENT DOCUMENTS 5,645,209 A * 7/1997 Green .............. A61B 17/07207
227/176.1
5,657,921 A　8/1997 Young et al.
(Continued)

FOREIGN PATENT DOCUMENTS

CN　101528151 A　9/2009
CN　102781353 A　11/2012
(Continued)

OTHER PUBLICATIONS

Extended European Search Report for Application No. EP24153514.5, mailed on Jun. 5, 2024, 12 pages.
(Continued)

*Primary Examiner* — Mark A Connolly
(74) *Attorney, Agent, or Firm* — Artegis Law Group, LLP

(57)　ABSTRACT

Techniques for control of an instrument include a device having an actuator. To perform an operation with an instrument coupled to the actuator, the instrument is operated according to a state machine by: transitioning the instrument from a gripped state to a clamped state in response to receiving a clamp command; transitioning the instrument from the clamped state to a firing state in response to receiving a fire command; transitioning the instrument from the firing state to a pause state in response to detecting a stall in the actuator used to actuate the instrument; transitioning
(Continued)

the instrument from the pause state to a stop firing state in response to a pause limit being reached; and transitioning the instrument from the pause state to the firing state in response to the actuator beginning to move again or after a first predetermined period of time has elapsed since entering the pause state.

20 Claims, 9 Drawing Sheets

Related U.S. Application Data continuation of application No. 16/072,356, filed as application No. PCT/US2017/015496 on Jan. 27, 2017, now Pat. No. 10,973,519.

(60) Provisional application No. 62/408,283, filed on Oct. 14, 2016, provisional application No. 62/288,784, filed on Jan. 29, 2016.

(51) Int. Cl.

| | |
|---|---|
| *A61B 17/072* | (2006.01) |
| *A61B 34/00* | (2016.01) |
| *A61B 34/10* | (2016.01) |
| *A61B 34/30* | (2016.01) |
| *A61B 34/35* | (2016.01) |
| *A61B 90/00* | (2016.01) |
| *A61B 34/20* | (2016.01) |
| *G05B 15/02* | (2006.01) |

(52) U.S. Cl.

CPC .............. *A61B 34/10* (2016.02); *A61B 34/30* (2016.02); *A61B 34/35* (2016.02); *A61B 34/74* (2016.02); *A61B 90/06* (2016.02); *A61B 2017/00017* (2013.01); *A61B 2017/00022* (2013.01); *A61B 2017/00039* (2013.01); *A61B 2017/00075* (2013.01); *A61B 2017/00128* (2013.01); *A61B 2017/00367* (2013.01); *A61B 2017/00398* (2013.01); *A61B 2017/0725* (2013.01); *A61B 2017/07257* (2013.01); *A61B 2017/07271* (2013.01); *A61B 2017/07278* (2013.01); *A61B 2034/2059* (2016.02); *A61B 34/25* (2016.02); *A61B 2034/305* (2016.02); *A61B 2090/064* (2016.02); *A61B 2090/066* (2016.02); *G05B 15/02* (2013.01)

(56) References Cited

U.S. PATENT DOCUMENTS

| | | | |
|---|---|---|---|
| 5,865,361 | A | 2/1999 | Milliman et al. |
| 6,651,034 | B1 | 11/2003 | Hedlund et al. |
| 6,793,652 | B1 | 9/2004 | Whitman et al. |
| 9,119,660 | B2 | 9/2015 | Rivers et al. |
| 10,828,030 | B2 | 11/2020 | Weir et al. |
| 10,973,519 | B2 | 4/2021 | Weir et al. |
| 11,291,442 | B2 | 4/2022 | Wixey et al. |
| 12,419,638 | B1 * | 9/2025 | Moubarak ............ A61B 17/068 |
| 2009/0069830 | A1 | 3/2009 | Mulvihill et al. |
| 2009/0090763 | A1 | 4/2009 | Zemlok et al. |
| 2011/0139851 | A1 | 6/2011 | Mccuen |
| 2012/0211542 | A1 | 8/2012 | Racenet |
| 2012/0248167 | A1 | 10/2012 | Flanagan et al. |
| 2013/0131650 | A1 | 5/2013 | Whitman et al. |
| 2013/0267950 | A1 | 10/2013 | Rosa et al. |
| 2014/0012289 | A1 | 1/2014 | Snow et al. |
| 2014/0039681 | A1 | 2/2014 | Bowling et al. |
| 2014/0110455 | A1 | 4/2014 | Ingmanson et al. |
| 2015/0100066 | A1 | 4/2015 | Kostrzewski et al. |
| 2015/0209573 | A1 | 7/2015 | Hibner et al. |
| 2015/0223812 | A1 | 8/2015 | Whitman et al. |
| 2015/0272583 | A1 | 10/2015 | Leimbach et al. |
| 2016/0066912 | A1 | 3/2016 | Baber et al. |
| 2017/0296183 | A1 | 10/2017 | Shelton, IV et al. |
| 2018/0049813 | A1 | 2/2018 | Yates et al. |
| 2021/0145441 | A1 | 5/2021 | Weir et al. |
| 2022/0183687 | A1 | 6/2022 | Wixey et al. |

FOREIGN PATENT DOCUMENTS

| | | | |
|---|---|---|---|
| EP | 2724674 | A2 | 4/2014 |
| EP | 2923653 | A2 | 9/2015 |
| EP | 2923657 | A1 | 9/2015 |
| EP | 2923661 | A2 | 9/2015 |
| EP | 3064152 | A1 | 9/2016 |
| EP | 3064153 | A2 | 9/2016 |
| EP | 3231373 | A2 | 10/2017 |
| EP | 3231375 | A1 | 10/2017 |
| EP | 3064152 | B1 | 11/2017 |
| JP | 2009090113 | A | 4/2009 |
| JP | 2014171879 | A | 9/2014 |
| WO | WO-2009123891 | A1 | 10/2009 |
| WO | WO-2012064528 | A1 | 5/2012 |
| WO | WO-2012068156 | A2 | 5/2012 |
| WO | WO-2012112249 | A1 | 8/2012 |
| WO | WO-2013059643 | A1 | 4/2013 |
| WO | WO-2014028702 | A1 | 2/2014 |
| WO | WO-2014127271 | A1 | 8/2014 |
| WO | WO-2014146107 | A1 | 9/2014 |
| WO | WO-2015142943 | A1 | 9/2015 |

OTHER PUBLICATIONS

Extended European Search Report for Application No. 17745032.7 mailed on Aug. 12, 2019, 11 pages.
Extended European Search Report for Application No. 17745046.7 mailed on Aug. 12, 2019, 11 pages.
Extended European Search Report for Application No. EP23174145.5, mailed on Sep. 5, 2023, 09 pages.
International Search Report and Written Opinion for Application No. PCT/US2017/015473, mailed on May 11, 2017, 11 pages.
International Search Report and Written Opinion for Application No. PCT/US2017/015496, mailed on May 1, 2017, 10 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

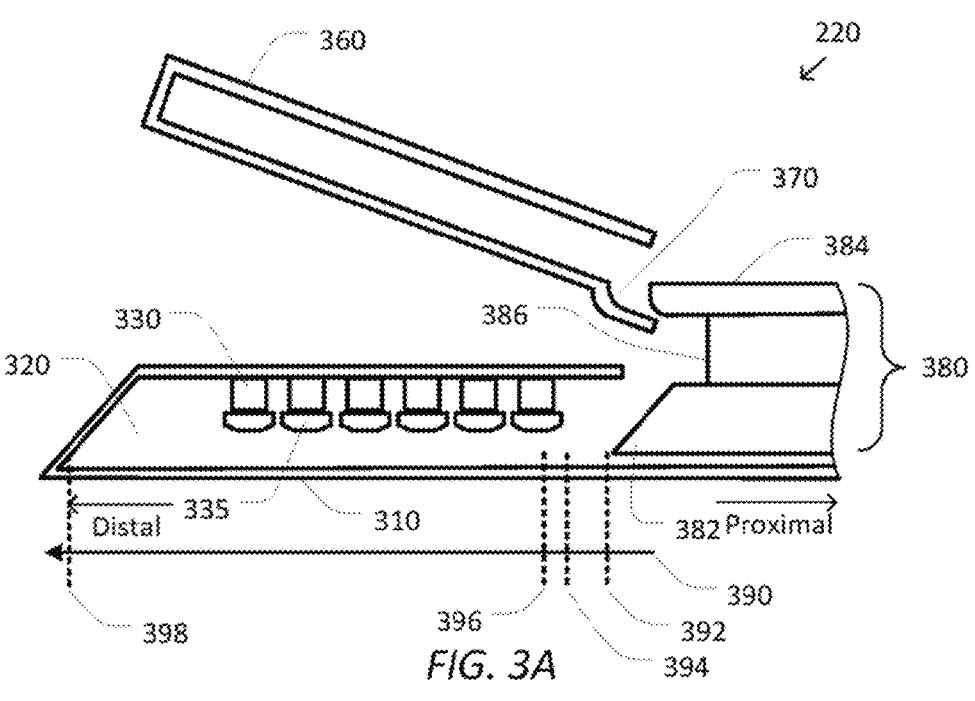
FIG. 3A
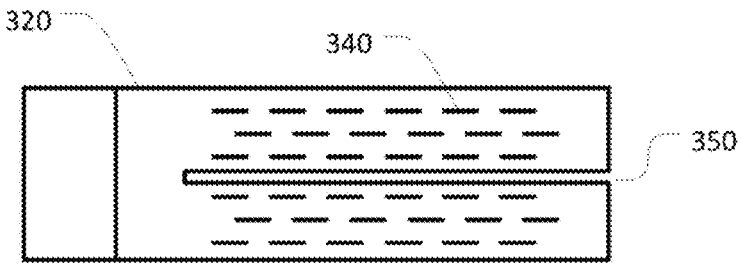
FIG. 3B
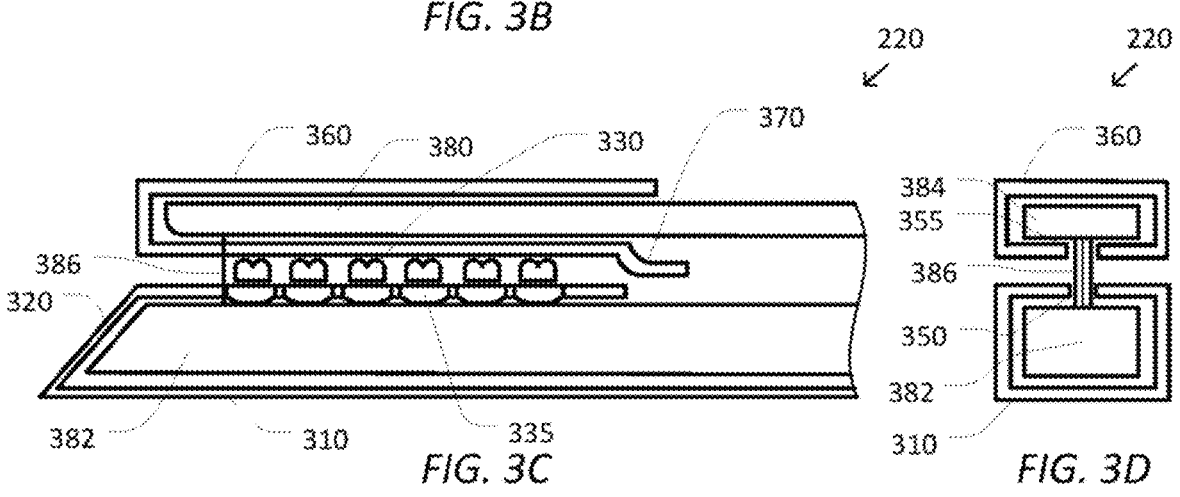
FIG. 3C
FIG. 3D

SYSTEM AND METHOD FOR VARIABLE VELOCITY INSTRUMENT

RELATED APPLICATIONS

This patent application is a continuation of U.S. patent application Ser. No. 17/160,288 filed on Jan. 27, 2021, which is a continuation of U.S. patent application Ser. No. 16/072,356 filed on Jul. 24, 2018, and now U.S. Pat. No. 10,973,519, which is a U.S. National Stage patent application of International Patent Application No. PCT/US2017/015496 filed on Jan. 27, 2017, the benefit of which is claimed, and claims priority to and the benefit of the filing date of U.S. Provisional Patent Application No. 62/288,784, entitled "System and Method for Variable Velocity Surgical Instrument" and filed Jan. 29, 2016 and U.S. Provisional Patent Application No. 62/408,283 entitled "I-Beam Stapler Controls Supplement" which was and filed Oct. 14, 2016. The disclosures of each of these related applications is incorporated by reference herein in its entirety.

This application is also related to International Patent Application No. PCT/US2017/015473 filed on Jan. 27, 2017.

TECHNICAL FIELD

The present disclosure relates generally to operation of devices with articulated arms and end effectors and more particularly to operation of a minimally invasive surgical instrument with a variable velocity control.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, traditional manual surgical instruments are being replaced by computer-assisted medical devices.

Minimally invasive surgical techniques using computer-assisted medical devices generally attempt to perform surgical and/or other procedures while minimizing damage to healthy tissue. Some minimally invasive procedures may be performed remotely through the use of computer-assisted medical devices with surgical instruments. With many computer-assisted medical devices, a surgeon and/or other medical personnel may typically manipulate input devices using one or more controls on an operator console. As the surgeon and/or other medical personnel operate the various controls at the operator console, the commands are relayed from the operator console to a patient side device to which one or more end effectors and/or surgical instruments are mounted. In this way, the surgeon and/or other medical personnel are able to perform one or more procedures on a patient using the end effectors and/or surgical instruments. Depending upon the desired procedure and/or the surgical instruments in use, the desired procedure may be performed partially or wholly under control of the surgeon and/or medical personnel using teleoperation and/or under semi-autonomous control where the surgical instrument may perform a sequence of operations based on one or more activation actions by the surgeon and/or other medical personnel.

Minimally invasive surgical instruments, whether actuated manually, teleoperatively, and/or semi-autonomously may be used in a variety of operations and/or procedures and may have various configurations. Many such instruments include an end effector mounted at a distal end of a shaft that may be mounted to the distal end of an articulated arm. In many operational scenarios, the shaft may be configured to be inserted (e.g., laparoscopically, thorascopically, and/or the like) through an opening (e.g., a body wall incision, a natural orifice, and/or the like) to reach a remote surgical site.

End effectors of different design and/or configuration may be used to perform different tasks, procedures, and functions so as to be allow the surgeon and/or other medical personnel to perform any of a variety of surgical procedures. Examples include, but are not limited to, cauterizing, ablating, suturing, cutting, stapling, fusing, sealing, etc., and/or combinations thereof. Accordingly, end effectors can include a variety of components and/or combinations of components to perform these surgical procedures.

Consistent with the goals of a minimally invasive procedure, the size of the end effector is typically kept small. One approach to keeping the size of the end effector small is to accomplish actuation of the end effector through the use of one or more inputs at a proximal end of the surgical instrument, where the proximal end is typically located externally to the patient. Various transmission components such as gears, levers, pulleys, cables, rods, belts, bands, and/or the like, may then be used to transmit actions from the one or more inputs along the shaft of the surgical instrument and to actuate the end effector. In the case of a computer-assisted, teleoperational medical device with an appropriate surgical instrument, a transmission mechanism at the proximal end of the instrument interfaces directly, or indirectly through other transmission components, with one or more actuators such as various motors, solenoids, servos, active actuators, hydraulics, pneumatics, and/or the like provided on an articulated arm of the patient side device or a patient side cart. The actuator(s) receive control signals produced in response to user commands provided through a master controller, and provide input to the instrument involving force and/or torque at the proximal end of the transmission mechanism; the various transmission elements ultimately transmit to actuate the end effector at the distal end of the transmission mechanism.

Because the size of the end effector is typically small, it may have a limited stiffness that may make is susceptible to flexing and/or splaying during some grasping, clamping, and/or stapling operations. Operating the instrument at a target velocity that is subject to a simple limit on the amount of applied torque and/or force applied to the transmission mechanism can often result in a grasping, clamping, and/or stapling operation with failed operations or a ragged velocity profile due to tissue variations over space or time, and different steps of the operation such as the different stages of forcing staples through the tissue in a stapling operation.

Accordingly, improved methods and systems for the operation of surgical instruments, such as a grasping, clamping, and/or stapling instruments, are desirable. In some examples, it may be desirable to reduce the amount of flexing and/or splaying of the instruments without unacceptably slowing down use of the instruments.

SUMMARY

Consistent with some embodiments, a surgical instrument for use with a computer-assisted medical device includes an end effector located at a distal end of the instrument, an actuator, and one or more drive mechanisms for coupling force or torque from the actuator to the end effector. To perform an operation with the instrument, the computer-assisted medical device is configured to set a velocity set point of the actuator to an initial velocity and monitor force or torque applied by the actuator. When the applied force or torque is above a first force or torque limit it is determined whether a continue condition for the operation is satisfied. When the continue condition is satisfied the operation is paused and when the continue condition is not satisfied it is determined whether forced firing of the actuator should take place.

Consistent with some embodiments, a method of operating a surgical instrument for use with a computer-assisted medical device includes one or more processors setting a velocity set point of an actuator to an initial velocity and measuring a force or torque applied by the actuator. When the applied force or torque is above a first force or torque limit, the method further includes determining, by the one or more processors, whether a continue condition for a stapling operation is satisfied. When the continue condition is satisfied, the method further includes pausing, by the one or more processors, further movement of the actuator. When the continue condition is not satisfied, the method further includes determining, by the one or more processors, whether forced firing of the actuator should take place.

Consistent with some embodiments, a non-transitory machine-readable medium comprising a plurality of machine-readable instructions which when executed by one or more processors associated with a computer-assisted medical device are adapted to cause the one or more processors to perform a method. The method includes setting a velocity set point of an actuator to an initial velocity and measuring a force or torque applied by the actuator. When the applied force or torque is above a first force or torque limit, the method further includes determining whether a continue condition for a stapling operation is satisfied. When the continue condition is satisfied, the method further includes pausing further movement of the actuator. When the continue condition is not satisfied, the method further includes determining whether forced firing of the actuator should take place.

BRIEF DESCRIPTION OF THE DRAWINGS

FIGS. 3A-3D are simplified diagrams of the end effector of FIG. 2 according to some embodiments.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Although the following description focuses primarily on embodiments of a combined grasping, stapling, and cutting surgical instrument, one of ordinary skill would understand that the variable velocity methods and mechanisms of the present disclosure may be applied to other medical instruments, including surgical and non-surgical instruments. Also, although the following description often discusses a medical device with robotically articulated arms (also "manipulators) for holding and actuating medical instruments, one of ordinary skill would understand that the methods and mechanisms of the present disclosure may also be used with computer-assisted medical instruments that are separate from robotic arms or articulated arms, including medical instruments designed to be hand-held or attached to non-articulated fixtures.

Figure 1:
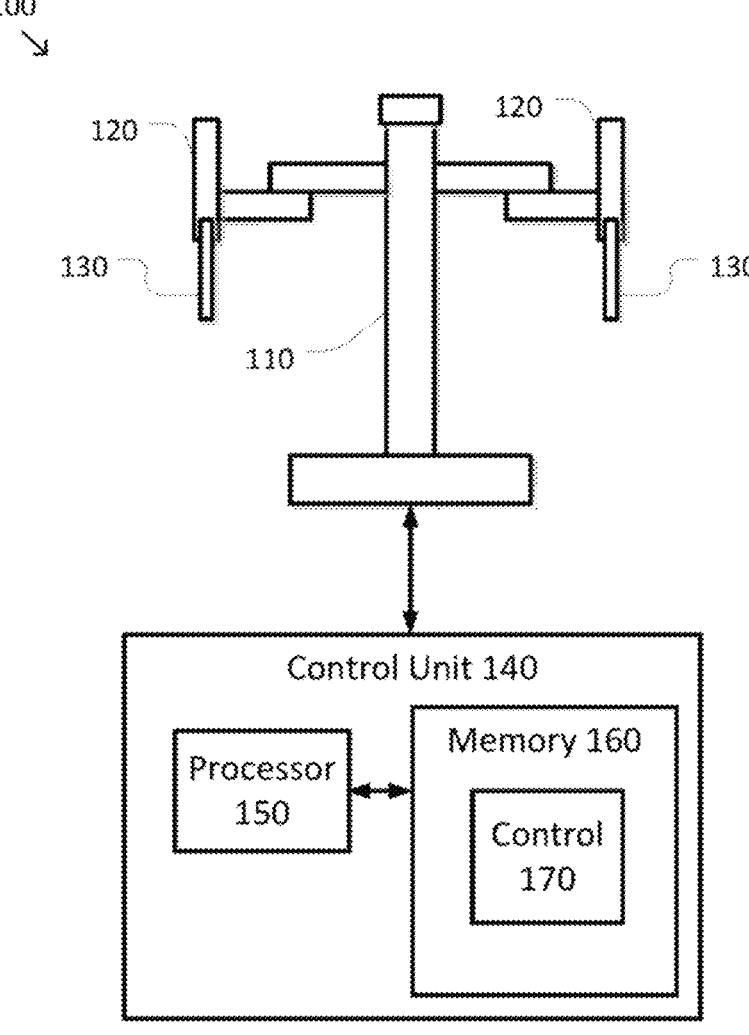
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a computer-assisted device 110 with one or more movable or articulated arms 120. Each of the one or more articulated arms 120 may support one or more instruments 130. In some examples, computer-assisted device 110 may be consistent with a computer-assisted surgical device. The one or more articulated arms 120 may each provide support for medical instruments 130 such as surgical instruments, imaging devices, and/or the like. Examples of medical instruments 130 include surgical instruments for interacting with tissue, imaging or sensing devices, and/or the like. In some examples, the instruments 130 may include end effectors that are capable of, but are not limited to, performing, gripping, retracting, cauterizing, ablating, suturing, cutting, stapling, fusing, sealing, etc., and/or combinations thereof.

Computer-assisted device 110 may further be coupled to an operator workstation (not shown), which may include one or more master controls for operating the computer-assisted device 110, the one or more articulated arms 120, and/or the instruments 130. In some examples, the one or more master controls may include master manipulators, levers, pedals, switches, keys, knobs, triggers, and/or the like. In some embodiments, computer-assisted device 110 and the operator workstation may correspond to a da Vinci® Surgical System commercialized by Intuitive Surgical, Inc. of Sunnyvale, California. In some embodiments, computer-assisted surgical devices with other configurations, fewer or more articulated arms, and/or the like may be used with computer-assisted system 100.

Computer-assisted device 110 is coupled to a control unit 140 via an interface. The interface may be wired and/or wireless, and may include one or more cables, fibers, connectors, and/or buses and may further include one or more networks with one or more network switching and/or routing devices. Operation of control unit 140 is controlled by processor 150. And although control unit 140 is shown with only one processor 150, it is understood that processor 150 may be representative of one or more central processing units, multi-core processors, microprocessors, microcontrollers, digital signal processors, field programmable gate arrays (FPGAs), application specific integrated circuits (ASICs), and/or the like in control unit 140. Control unit 140 may be implemented as a stand-alone subsystem and/or board added to a computing device or as a virtual machine. In some embodiments, control unit 140 may be included as part of the operator workstation and/or operated separately from, but in coordination with the operator workstation.

Memory 160 may be used to store software executed by control unit 140 and/or one or more data structures used during operation of control unit 140. Memory 160 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown in FIG. 1, memory 160 includes a control application 170 that may be used to support autonomous, semiautonomous, and/or teleoperated control of computer-assisted device 110. Control application 170 may include one or more application programming interfaces (APIs) for receiving position, motion, force, torque, and/or other sensor information from computer-assisted device 110, articulated arms 120, and/or instruments 130, exchanging position, motion, force, torque, and/or collision avoidance information with other control units regarding other devices, and/or planning and/or assisting in the planning of motion for computer-assisted device 110, articulated arms 120, and/or instruments 130. In some examples, control application 170 further supports autonomous, semiautonomous, and/or teleoperated control of the instruments 130 during a surgical procedure. And although control application 170 is depicted as a software application, control application 170 may optionally be implemented using hardware, software, and/or a combination of hardware and software.

In some embodiments, computer-assisted system 100 may be found in an operating room and/or an interventional suite. And although computer-assisted system 100 includes only one computer-assisted device 110 with two articulated arms 120 and corresponding instruments 130, one of ordinary skill would understand that computer-assisted system 100 may include any number of computer-assisted devices with articulated arms and/or instruments of similar and/or different in design from computer-assisted device 110. In some examples, each of the computer-assisted devices may include fewer or more articulated arms and/or instruments.

Figure 2:
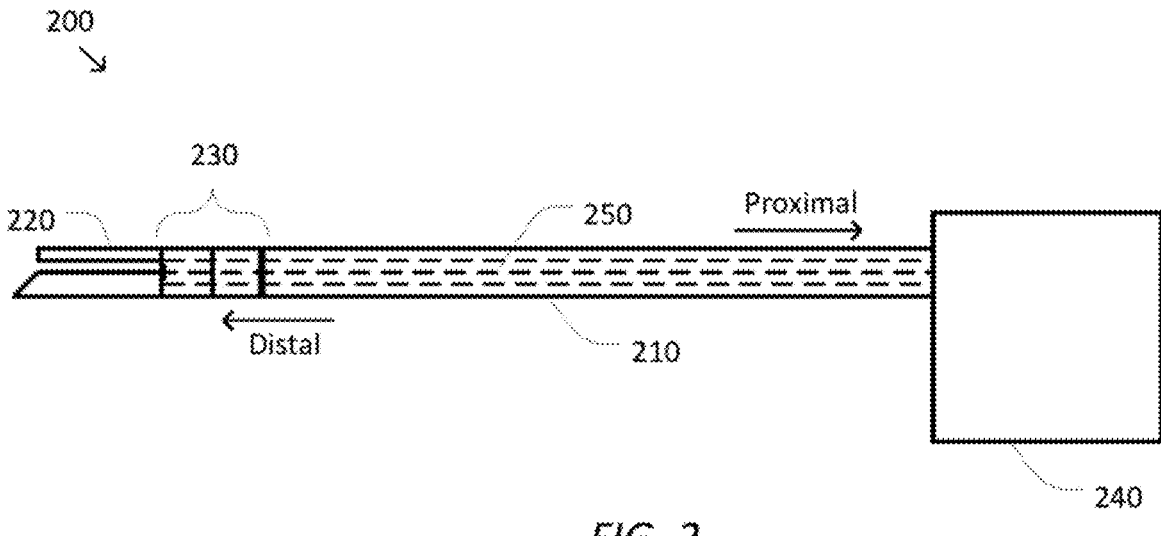
FIG. 2 is a simplified diagram showing a minimally invasive surgical instrument according to some embodiments.

FIG. 2 is a simplified diagram showing a minimally invasive surgical instrument 200 according to some embodiments. In some embodiments, surgical instrument 200 may be consistent with any of the instruments 130 of FIG. 1. The directions "proximal" and "distal" as depicted in FIG. 2 and as used herein help describe the relative orientation and location of components of surgical instrument 200. Distal generally refers to elements in a direction further along a kinematic chain from a user or machine holding the instrument 200, a base of a computer-assisted device for holding the instrument 200, such as computer-assisted device 110, and/or or closest to the surgical work site in the intended operational use of the surgical instrument 200. Proximal generally refers to elements in a direction closer along a kinematic chain toward the base of the computer-assisted device, a user or machine holding the instrument 200, and/or one of the articulated arms of the computer-assisted device for holding the instrument 200.

As shown in FIG. 2, surgical instrument 200 includes a long shaft 210 coupling an end effector 220 located at a distal end of shaft 210 to where the surgical instrument 200 is mounted to an articulated arm and/or a computer-assisted device at a proximal end of shaft 210. Depending upon the particular procedure for which the surgical instrument 200 is being used, shaft 210 may be inserted through an opening in a patient (e.g., a body wall incision, a natural orifice, and/or the like) in order to place end effector 220 in proximity to a remote surgical site located within the anatomy of a patient. As further shown in FIG. 2, end effector 220 is generally consistent with a two-jawed gripper-style end effector, which in some embodiments may further include a cutting and/or a stapling mechanism as is described in further detail below with respect to FIGS. 3A-3D. However, one of ordinary skill would understand that different surgical instruments 200 with different end effectors 220, such as end effectors with fasteners other than staples, are possible and may be consistent with the embodiments of surgical instrument 200 as described elsewhere herein.

A surgical instrument, such as surgical instrument 200 with end effector 220 typically uses multiple degrees of freedom (DOFs) during its operation. Depending upon the configuration of surgical instrument 200 and the articulated arm and/or computer-assisted device to which it is mounted, various DOFs that may be used to position, orient, and/or operate end effector 220 are possible. In some examples, shaft 210 may be inserted in a distal direction and/or retreated in a proximal direction to provide an insertion DOF that may be used to control how deep within the anatomy of the patient that end effector 220 is placed. In some examples, shaft 210 may be able rotate about its longitudinal axis to provide a roll DOF that may be used to rotate end effector 220. In some examples, additional flexibility in the position and/or orientation of end effector 220 may be provided by one or more joints and/or links, such as the joints and links of an articulated arm 120, located proximal to shaft 210 and surgical instrument 200. In some examples, an optional articulated wrist 230 may be used to couple end effector 220 to the distal end of shaft 210. In some examples, articulated wrist 230 may optionally include one or more rotational joints, such as one or more roll, pitch or yaw joints that may provide one or more "roll," "pitch," and "yaw" DOF(s), respectively, that may be used to control an orientation of end effector 220 relative to the longitudinal axis of shaft 210. In some examples, the one or more rotational joints may include a pitch and a yaw joint; a roll, a pitch, and a yaw joint, a roll, a pitch, and a roll joint; and/or the like. In some examples, end effector 220 further includes a grip DOF used to control the opening and closing of the jaws of end effector 220 and/or an activation DOF used to control the extension, retraction, and/or operation of a stapling and cutting mechanism as is described in further detail below.

Surgical instrument 200 further includes a drive system 240 located at the proximal end of shaft 210. Drive system 240 includes one or more components for introducing forces and/or torques to surgical instrument 200 that can be used to manipulate the various DOFs supported by surgical instrument 200. In some examples, drive system 240 may optionally include one or more motors, solenoids, servos, active actuators, hydraulics, pneumatics, and/or the like that are operated based on signals received from a control unit, such as control unit 140 of FIG. 1. In some examples, the signals may include one or more currents, voltages, pulse-width modulated wave forms, and/or the like. In some examples, drive system 240 may optionally include one or more shafts, gears, pulleys, rods, bands, and/or the like which may be coupled to corresponding motors, solenoids, servos, active actuators, hydraulics, pneumatics, and/or the like that are part of the articulated arm, such as any of the articulated arms 120, to which surgical instrument 200 is mounted. In some examples, the one or more drive inputs, such as shafts, gears, pulleys, rods, bands, and/or the like, are used to receive forces and/or torques from the motors, solenoids, servos, active actuators, hydraulics, pneumatics, and/or the like and apply those forces and/or torques to adjust the various DOFs of surgical instrument 200. In this discussion, both "force" and "torque" are sometimes used individually to indicate linear force, rotational torque, and/or both, as applicable.

In some embodiments, the forces and/or torques generated by and/or received by drive system 240 are transferred from drive system 240 and along shaft 210 to the various joints and/or elements of surgical instrument 200 located distal to drive system 240 using one or more drive mechanisms 250. In some examples, the one or more drive mechanisms 250 may optionally include one or more gears, levers, pulleys, cables, rods, bands, and/or the like. In some examples, shaft 210 is hollow and the drive mechanisms 250 pass along the inside of shaft 210 from drive system 240 to the corresponding DOFs in end effector 220 and/or articulated wrist 230. In some examples, each of the drive mechanisms 250 may optionally be a cable disposed inside a hollow sheath or lumen in a Bowden cable like configuration. In some examples, the cable and/or the inside of the lumen may optionally be coated with a low-friction coating such as polytetrafluoroethylene (PTFE) and/or the like. In some examples, as the proximal end of each of the cables is pulled and/or pushed inside drive system 240, such as by wrapping and/or unwrapping the cable about a capstan or shaft, the distal end of the cable moves accordingly and applies a suitable force and/or torque to adjust one or more of the DOFs of end effector 220, articulated wrist 230, and/or surgical instrument 200.

FIGS. 3A-3D are simplified diagrams of end effector 220 according to some embodiments. As shown in FIGS. 3A-3D, the distal end of surgical instrument 200 or end effector 220 includes a mechanism for jaw closure, tissue stapling, and tissue cutting. And although end effector 220 is shown and described with one fixed and one movable jaw, one of ordinary skill would understand that the distal end of surgical instrument 200 could be modified to use two movable jaws. It should be further understood that although the description below is in the context of a clamping, stapling, and cutting instrument that simultaneously clamps, staples, and cuts tissue, the aspects so described may be applicable to instruments with or without cutting features, instruments supporting fusing rather than stapling, and/or the like.

FIG. 3A shows a cut-way side view of end effector 220 prior to actuation so that the jaws of end effector 220 are shown in an open position. As shown, end effector includes a first jaw 310 that is generally fixed. Jaw 310 is designed to receive a replaceable staple cartridge 320 holding a plurality of staples 330 and a plurality of staple pushers 335. Staple cartridge 320 is designed to be replaceable so that end effector 220 is reusable by removing a first staple cartridge 320 after one or more of the staples 330 are used and replacing it with a second staple cartridge 320 having a new set of staples 330 that can be used to further perform the surgical procedure. FIG. 3B shows a top view of staple cartridge 320. As depicted in FIG. 3B, staple cartridge include six rows of staple slots 340 through which staples 330 may be applied to clamped tissue upon actuation of end effector 220. The rows of staple slots 340 include three rows on each side of a cutting slot 350, which is described in further detail below. Placing staples 330 on both sides of cutting slot 350 allows for the application of staples 330 to both sides of a desired cutting line so as to close the tissue on both sides of the cutting line. The rows of staple slots 340 are also offset relative to each other to provide more complete tissue closure along both sides of the cutting line. And although, staple cartridge 320 is shown with six rows of offset staple slots 340, each having six staple slots 340 of uniform size, one of ordinary skill would understand that fewer or more rows of staple slots with fewer or more staples, staple slots of varying size, and staple slots of varying patterns are possible.

As further shown in FIG. 3A, end effector 220 further includes a second jaw 360 that is movable about a pivot point (not shown) near its proximal end. In the context of a stapling instrument, second jaw 360 may alternatively be referred to as anvil 360. In the embodiments shown in FIG. 3A, anvil 360 includes a transitional edge 370 configured so that upon initial actuation of end effector 220, a gap between anvil 360 and jaw 310 is rapidly reduced until tissue is clamped between anvil 360 and jaw 310. Actuation of end effector 220 is accomplished by movement of a reciprocating element 380 from the proximal end of end effector 220 to the distal end of end effector 220. Reciprocating element 380 is coupled to the distal end of one or more of the drive mechanisms 250.

Reciprocating element 380 includes a sled 382 and a flange 384 with a cutting blade 386 coupled between the sled 382 and flange 384. Reciprocating element 380 has a general I-beam style cross-sectional shape as shown in the cut-away end view of end effector 220 shown in FIG. 3D. As end effector 220 is actuated for stapling, sled 382 is propelled along within jaw 310 and staple cartridge 320 as reciprocating element 380 is pushed by drive mechanism 250. Sled 382 includes a wedge-shaped leading or distal end such that, as the leading end encounters each of the staple pushers 335, the leading end pushes the staple pushers 335 against corresponding staples 330. This action results in the firing of each of the staples 330 through a respective one of the staple slots 340. Although sled 382 is shown with a single wedge at its leading edge, sled 382 may optionally include separate wedges for each of the rows of staples 330 and staple pushers 335 in staple cartridge 320. Additionally, each of the separate wedges may optionally be staggered relative to each other in the direction of sled 382 movement. In some embodiments, staple pushers 335 are optional and the leading edge of sled 382 pushes directly against staples 330. As sled 382 is being propelled along within jaw 310 and staple cartridge 320, flange 384 is propelled along within anvil 360. As the leading distal end of flange 384 encounters transitional edge 370, flange 384 causes initial rapid closure of the gap between anvil 360 and jaw 310. Cutting blade 386 is located somewhat proximally to the distal ends of sled 382 and flange 384 so that cutting of any clamped tissue trails the firing of the staples 330 along both sides of the cutting line. As reciprocating element 380 is actuated, cutting blade 386 travels along cutting slot 350 as well as a corresponding cutting slot 355 located in anvil 360.

FIGS. 3C and 3D show a cut-away side and a cut-away end view, respectively, of end effector 220 after it has been fully actuated. As shown, reciprocating element 380, along with sled 382, flange 384, and cutting blade 386, is located at the distal end of end effector 220. As the leading edge of sled 382 encounters each of the staple pushers 335, it pushes the staple pushers 335 which in turn push the staples 330 up through respective staple slots 340 where they are pressed through any clamped tissue into a face of anvil 360 where they are bent into final shape as shown in FIG. 3C. The gap between anvil 360 and jaw 310 is maintained by the presence of flange 384 within anvil 360. In this way, reciprocating element 380, sled 382, flange 384, and cutting blade 386 are all components of end effector 220 which move in response to applied force or torque provided by the actuator controlling movement of reciprocating element 380.

Operation of end effector 220 is subject to several practical considerations as it is actuated. Initially, reciprocating element 380 can be moved distally at a high level of velocity with very little force or torque having to be applied to the drive mechanism 250 used to propel reciprocating element 380. However, as flange 384 begins to encounter leading edge 370 and the gap between anvil 360 and jaw 310 begins to rapidly close, any tissue clamped between anvil 360 and jaw 310 begins to resist further movement of reciprocating element 380. To compensate for this, drive system 240 applies additional force and/or torque to drive mechanism 250 to maintain the velocity of reciprocating element 380. Monitoring of the force and/or torque occurs to make certain that a reasonable upper limit is maintained on the applied force and/or torque to avoid unacceptable flexing and/or splaying of jaw 310 and/or anvil 360; damage to end effector 220, drive system 240, and/or drive mechanism 250; and/or damage to the clamped tissue. Second, as the tissue is clamped between anvil 360 and jaw 310, it typically begins to desiccate as fluids are pushed out of the tissue due to the pressure of the clamping. As long as the velocity of reciprocating element 380 is appropriately controlled, the amount of force and/or torque to continue advancing reciprocating element 380 can generally be managed within reasonable limits for compliant tissue. Third, additional force and/or torque is typically needed so that sled 382 can push each of the staple pushers 335 against the staples 330 so that the staples 330 are pushed through the clamped tissue and/or cutting blade 386 can cut the clamped tissue, while maintaining a desired velocity for reciprocating element 380. This additional force and/or torque may vary significantly as properties of the tissue being stapled change, previously applied staple lines are crossed, and/or the like.

To achieve a smooth operation of end effector 220, it is generally desired to actuate reciprocating element 380 with a constant velocity throughout initial contact with the tissue, firing of staples 330, and cutting of the clamped and stapled tissue. In some embodiments, this occurs with monitoring and/or limiting the applied force and/or torque so as to reduce and/or avoid unacceptable flexing and/or splaying of jaw 310 and/or anvil 305; damage to end effector 220, drive system 240, and/or drive mechanism 250; and/or damage to the clamped tissue. One approach is to operate end effector 220 using a constant velocity set point subject to a maximum force and/or torque limit on drive system 240. The constant velocity set point can be selected to provide a balance between speed of operation and risk of encountering the force and/or torque limit. In some examples, the constant velocity set point may optionally be adjustable, such as by an operator, based on a type of tissue that is being clamped, stapled, and clamped. In some embodiments and/or under certain operating conditions, particular velocity set points and/or ranges of velocity set points may result in less than optimal operation of end effector 220 either due to a too low constant velocity set point, ragged operation due to constant encounters with the force and/or torque limit that cause the reciprocating element 380 to slow down and speed up in a possibly erratic pattern, and/or the like.

Improved performance of end effector 220 and a smoother operation are possible using a velocity profile for reciprocating element 380 that adapts based on the force and/or torque being applied by drive system 240 and drive mechanism 250. For example, as forces and/or torques begin to increase, the velocity of reciprocating element 380 is decreased in a controlled fashion, and as forces and/or torques begin to decrease, the velocity of reciprocating element 380 is increased in a controlled fashion. In this way smoother operation of end effector 220 is obtained compared to relying on a single force and/or torque limit to indirectly slow down the velocity of reciprocating element 380. For example, slowing down when a force and/or torque threshold lower than a maximum force and/or torque limit may result in operation with fewer starts and stops as the reciprocating element 380 bogs down at the maximum force and/or torque limit.

According to some embodiments, other techniques may be used for adjusting velocity. For example, as forces and/or torques pass a threshold amount, the velocity of reciprocating element 380 may be set to a current detected velocity of reciprocating element 380 and/or a velocity set point slightly lower than the current detected velocity.

Referring back to FIG. 3A, also shown in is an arrow 390 indicating the direction of travel of reciprocating element 380 during actuation of an example stapling process. A set of dotted lines 392, 394, 396, 398 indicate particular locations that the distal tip of sled 382 reaches during a stapling operation. When the distal tip of sled 382 is located between the location indicated by dotted lines 392 and 394, the stapler is in a "gripping" state (also "gripping stage"), in which first jaw 310 and second jaw 360 close to a roughly parallel posture and can be lightly gripping patient tissue. As the distal tip of sled 382 reaches the location indicated by dotted line 394, the stapler transitions from the gripping state to a "clamping-not-yet-firing" state (also "clamping-not-yet-firing stage"), in which first jaw 310 and second jaw 360 are held in close enough proximity so as to exert substantive clamping force on the patient tissue. This clamping-not-yet-firing state can provide some pre-stapling compression of the patient tissue, and help flatten the tissue to improve the chances of a successful stapling operation.

As the distal tip of sled 382 reaches the location indicated by dotted line 396, the stapler has transitioned from the clamping-not-yet-firing state to the "firing" state (also "firing stage"), in which sled 382 pushes various ones of staple pushers 335 against corresponding staples 330 and fires these staples 330 through staple slots 340. The stapling process ends when the distal tip of sled 382 has reached its goal at the location indicated by dotted line 398. This firing state may also be termed a "clamping" state that is separate from the clamping-not-yet-firing state.

According to some embodiments, the applied force or torque may be monitored during the firing state, the clamping-not-yet-firing state, the gripping state, and/or a combination of any two or three of these states. In some examples, applied force or torque may be monitored and processes performed, such as those discussed in this disclosure, in the firing state. In some examples, applied force or torque may be monitored and processes performed, such as those discussed in this disclosure, in the firing state and all or part of the clamping-not-yet-firing state. In some examples, different force or torque limit thresholds and/or use other parameters may be used for the firing and clamping-not-yet-firing states.

According to some embodiments, feedback may be provided to a surgeon and/or other medical personnel during the stapling operation. In some examples, a control unit in a computer-assisted system (e.g., computer-assisted system 100) may estimate the likelihood of a successful stapling process in the clamping-not-yet-firing state and provide such estimate to users through any appropriate method, including through visual displays, auditory feedback, and/or the like. In some examples, this feedback may be provided while the stapling process can be readily reversed, so that no staples are expended and can be used elsewhere during a procedure. In some embodiments, the computer-assisted system will inhibit the start of the firing state until the likelihood of successful stapling is gauged to be sufficiently high.

In some embodiments, surgical instrument 200 and/or associated computer-assisted system (e.g., computer-assisted system 100) is configured with user interfaces that make these three states distinctive to the operator. For example, some embodiments provide different controls for changing states through different combinations of knobs, buttons, switches, pedals, and other input devices. In some examples, for a teleoperational computer-assisted system, this computer-assisted system may be configured to do the following: (1) command entry into the gripping state, such as by commanding sled 382 move to a location corresponding to dotted line 392 at a gripping velocity, in response to sensing a pinching input on a master manipulator input device associated with an active stapler instrument, (2) command entry into the clamping-not-yet-firing state, such as by commanding sled 382 move to a location corresponding to dotted line 394 at a clamping-not-yet-firing velocity, in response to a depression of a first pedal, (3) command entry into the firing state and continuation into the firing state, such as by commanding sled 382 move to a location past dotted line 396, to dotted line 398 at the distal end of end effector 220, at a firing velocity. Some embodiments may also be configured with timeouts, such that the pinching motion, depression of the first pedal, and/or depression of the second pedal result in commands for the associated states after associated predetermined periods of time have passed with the pinching motion, first pedal depression, and/or second pedal depression. In some embodiments, surgical instrument 200 or associated computer-assisted system (e.g., computer-assisted system 100) is configured with user interfaces that combine from the user control perspective the gripping and clamping-not-yet-firing states, or the "camping-not-yet-firing" and firing states. In some embodiments, a single switch or pedal is provided for the operator to instruct entry into the gripping state and transition to the clamping-not-yet-firing state. In some embodiments, a single switch or pedal is provided for the operator to instruct entry into the clamping-not-yet-firing state and transition to the firing state.

Figure 4:
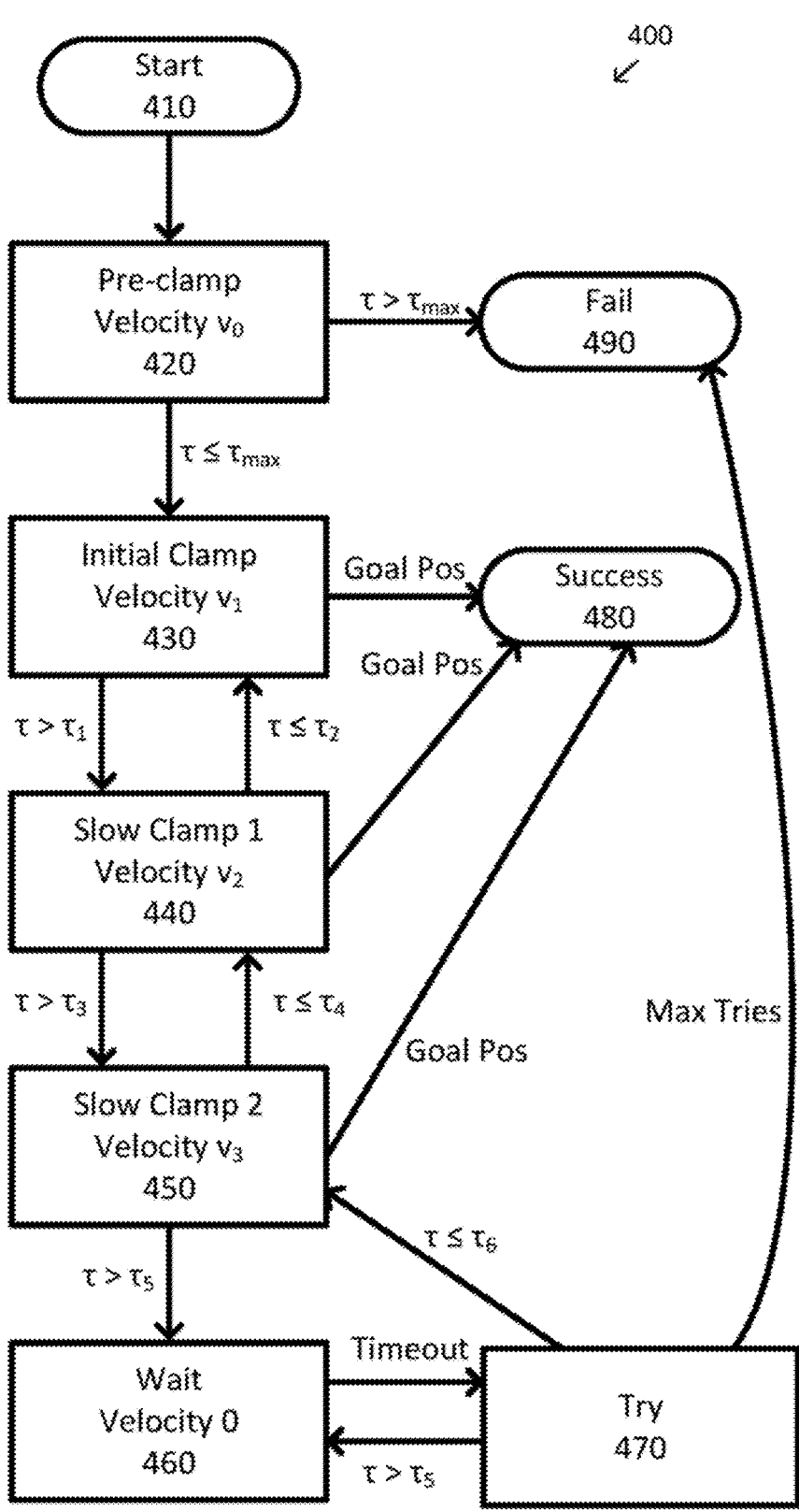
FIG. 4 is a simplified diagram of a state machine for operating an end effector according to some embodiments.

FIG. 4 is a simplified diagram of a state machine 400 for operating an end effector according to some embodiments. One or more of the states 410-490 of state machine 400 may be implemented, at least in part, in the form of executable code stored on non-transient, tangible, machine readable media. This executable code, when run by one or more processors (e.g., the processor 150 in control unit 140), may cause the one or more processors to implement one or more of the states 410-490. In some embodiments, state machine 400 may be implemented by an application, such as control application 170. In some embodiments, state machine 400 may be used to restrict and/or limit the velocity set point of an actuator, such as the actuator controlling movement of reciprocating element 380, based on the torque being applied by the actuator. In some embodiments, while state machine 400 is operating, the torque of the actuator is monitored. In some embodiments, state transitions between states 410-490 may occur when the indicated state transitions occur or optionally may occur at periodic intervals based on execution of a control loop implementing state machine 400.

State machine 400 begins in a start state 410. Upon direction and/or command of an operator, such as a surgeon, via the activation of one or more controls, inputs, and/or the like, operation of the end effector transitions to a pre-clamp state 420. In pre-clamp state 420, a velocity set point of the actuator, such as the actuator propelling reciprocating element 380, is set to an initial velocity $v_0$. In some examples, velocity $v_0$ may optionally be consistent with a maximum allowed velocity for the actuator. In some embodiments, operation of the end effector remains in pre-clamp state 420 until the actuator has moved a minimum distance or reached an initial position (e.g., the position corresponding to dotted line 394). In some examples, the minimum distance may correspond to a position where initial clamping of tissue occurs, such as slightly before and/or after the distal end of flange 384 encounters transitional edge 370 and the gap between anvil 360 and jaw 310 begins to close. In some embodiments, this initial clamping of tissue is associated with the "gripping" state discussed in conjunction with FIG. 3A and/or a before-gripping state applicable just before the gripping state. In some embodiments, this initial clamping of tissue is associated with part or all of the gripping and clamping-not-yet-firing states discussed in conjunction with FIG. 3A. When the torque of the actuator exceeds a maximum torque, $\tau_{max}$, before reaching the minimum distance, state machine 400 transitions to a fail state 490. State machine 400 may indicate the fail state 490 to human operators visually, aurally, or via some other feedback method. When the torque of the actuator does not exceed the maximum torque, state machine 400 transitions to an initial clamp state 430.

In the initial clamp state 430, the velocity set point of the actuator is set to an initial clamp velocity $v_1$. Control of the actuator then continues at velocity $v_1$ until either a goal position is reached, such as when reciprocating element 380 has been propelled to the distal end of end effector 220 or a torque threshold $\tau_1$ is reached. Torque $\tau_1$ is lower than the maximum torque $\tau_{max}$. In some examples, velocity $v_1$ may optionally be the same velocity as the initial velocity $v_0$. State machine 400 may indicate the success state 480 to human operators visually, aurally, and/or via some other feedback method. When the goal position is reached, state machine 400 transitions to a success state 480. When the torque of the actuator exceeds torque $\tau_1$ before the goal position is reached, state machine 400 transitions to a first slow clamp state 440.

In the first slow clamp state 440, the velocity set point of the actuator is set to a velocity $v_2$ lower than velocity $v_1$. Control of the actuator then continues at velocity $v_2$. While in the first slow clamp state 440, the torque of the actuator is further monitored to see whether it is increasing or decreasing. When the torque of the actuator decreases to a torque $\tau_2$, which is lower than torque $\tau_1$ (such as 5-20% lower than $\tau_1$ and/or 1-3 N-m RANGE below $\tau_1$) state machine 400 transitions back to initial clamp state 430, where the velocity set point of the actuator is increased back to velocity $v_1$. The amount to which torque $\tau_2$ is lower than torque $\tau_1$ may be set to introduce hysteresis in the velocity control of the actuator to avoid excess thrashing of the velocity set point for the actuator. When the torque of the actuator increases to torque $\tau_3$, state machine 400 transitions to a second slow clamp state 450. Torque $\tau_3$ is lower than the maximum torque $\tau_{max}$, but is typically higher than torque $\tau_1$ so that increasing torques continue to result in lower velocity set points for the actuator. When the goal position is reached, state machine 400 transitions to success state 480.

In the second slow clamp state 450, the velocity set point of the actuator is set to a velocity $v_3$ lower than velocity $v_2$. Control of the actuator then continues at velocity $v_3$. While in the second slow clamp state 450, the torque of the actuator is further monitored to see whether it is increasing or decreasing. When the torque of the actuator decreases to a torque $\tau_4$, which is lower than torque $\tau_3$, state machine 400 transitions back to the first slow clamp state 440, where the velocity of the actuator is increased. The amount to which torque $\tau_4$ is lower than torque $\tau_3$ may be set to introduce hysteresis in the velocity control of the actuator to avoid excess thrashing of the velocity set point for the actuator. When the torque of the actuator increases to torque $\tau_5$, state machine 400 transitions to a wait state 460. Torque $\tau_5$ may optionally be the same or lower than the maximum torque $\tau_{max}$, but is typically higher than torque $\tau_3$ so that increasing torques continue to result in lower velocity set points for the actuator. When the goal position is reached, state machine 400 transitions to success state 480.

In wait state 460, state machine 400 pauses the operation for a predetermined period of time (also called a "pause period"). To pause the operation in wait state 460, state machine 400 may pause the actuator by setting the velocity set point of the actuator to zero to cease movement of the actuator. In some examples, setting the velocity set point of the actuator to zero allows for additional time in which the clamped tissue may further desiccate. In some examples, state machine 400 remains in wait state for a predetermined period of time, to provide a temporal pause from stapler actuation. In some examples, the predetermined period of time may optionally be implemented using a hardware and/or software timer. After the predetermined period of time times out, state machine 400 automatically transitions to a try state 470.

In the try state 470, an attempt to move the actuator is made. Each time a try is attempted, a try counter is increased. In some examples, the attempt may optionally include setting the velocity set point of the actuator back to velocity $v_3$ or another velocity value. When movement of the actuator is possible and the torque of the actuator remains below a torque $\tau_6$, which is lower than torque $\tau_5$, the try counter is reset to zero and state machine 400 transitions back to the second slow clamp state 450, where the velocity set point of the actuator is increased back to velocity $v_3$. The amount to which torque $\tau_6$ is lower than torque $\tau_5$ may be set to introduce hysteresis in the velocity control of the actuator to avoid excess thrashing of the velocity set point for the actuator. When the torque of the actuator remains above torque $\tau_6$, during try state 460, state machine 400 returns to wait state 460 to wait an additional amount of time. State machine 400 may be configured such that it can transition to wait state 460 only after a try period of time has passed, a minimum try distance has been achieved, and/or both. When the try counter exceeds a maximum number of tries, state machine 400 transitions to fail state 490.

In success state 480, successful stapling and cutting is detected and control of the actuator is optionally reversed so that the jaws of the end effector open with a corresponding release of the clamped tissue. In the examples, of FIGS. 3A-3D, reversing the actuator includes pulling reciprocating element 380 in the proximal direction so that sled 382 is pulled out of jaw 310 and staple cartridge 320, flange 384 is pulled out of anvil 360 allowing anvil 360 to pivot open, and cutting blade 386 is pulled back into a safety position, such as a garaged position. In some examples, success of the stapling and cutting operation may optionally be reported to the operator using an audio and/or visual alert.

In fail state 490, failure to complete the stapling and cutting operation is detected because the actuator was not able to reach the goal position. In the examples of FIGS. 3A-3D, this occurs when reciprocating element 380 is not able to be propelled to the distal end of jaw 310 and anvil 360. While in fail state 490, an audio and/or visual alert is reported to the operator indicating failure of the stapling and cutting operation. In some examples, reversing of the actuator may optionally be attempted, either automatically by the state machine or at the express command of the operator.

As discussed above and further emphasized here, FIG. 4 is merely an example which should not unduly limit the scope of the claims. One of ordinary skill in the art would recognize many variations, alternatives, and modifications. In some embodiments, properties of the end effector and the actuator other than torque may alternatively be monitored and result in the state transitions described above. In some examples, force applied by the actuator may be monitored instead of torque. In some embodiments, initial clamp state 430 and pre-clamp state 420 may optionally be combined into a single state. In some embodiments, the second slow clamp state 450 may be removed, such that state machine 400 transitions from the first slow clamp state 400 to wait state 460 when the torque of the actuator is higher than torque $\tau_3$. In some embodiments, the first slow clamp state 440 and the second slow clamp state 450 are removed, such that the process transitions from initial clamp state 430 to wait state 460 when the torque of the actuator is higher than torque $\tau_1$. In some embodiments, additional slow clamp states may optionally be added between the second slow clamp state 450 and wait state 460 depending upon how many steps are desired in the velocity-torque profile for the end effector.

In some embodiments, one or more techniques may optionally be used to reduce the effects of temporary transients in the application of the torque thresholds. In some examples, the state transitions of state machine 400 occur when the applied torque remains above or below the corresponding torque threshold for a predetermined period of time. In some examples, the predetermined period of time may optionally be different for torque thresholds that decrease the velocity set point and torque thresholds that increase the velocity set point. In some examples, the state transitions of state machine 400 occur when an average value of the applied torque is above or below the corresponding torque threshold. In some examples, the average is computed using exponential smoothing. In some examples, the applied torque is low-pass filtered.

Figure 5:
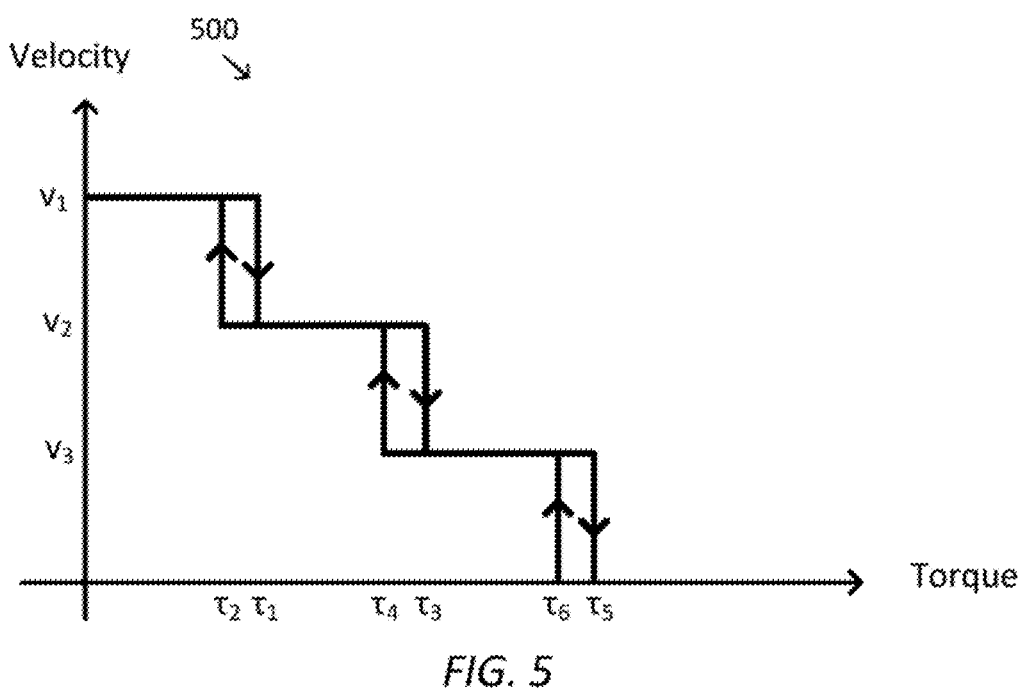
FIG. 5 is a simplified diagram of a velocity-torque profile an end effector according to some embodiments.

FIG. 5 is a simplified diagram of a velocity-torque profile 500 for the end effector of FIG. 3 according to some embodiments. As shown in FIG. 5, velocity-torque profile 500 includes multiple velocity settings that vary based on a monitored torque. In some examples, velocity-torque profile

500 is consistent with the velocity set points implemented by state machine 400. In velocity-torque profile 500, the velocity set point of an actuator, such as the actuator for end effector 220, is set to velocity $v_1$ until the torque applied by the actuator exceeds torque $\tau_1$. Once torque $\tau_1$ is exceeded, the velocity set point is reduced to velocity $v_2$. The velocity of the actuator is then controlled at velocity $v_2$ until the torque applied by the actuator exceeds torque $\tau_3$. Once torque $\tau_3$ is exceeded, the velocity set point is reduced to velocity $v_3$. The velocity of the actuator is then controlled at velocity $v_3$ until the torque applied by the actuator exceeds torque $\tau_5$. Once torque $\tau_5$ is exceeded, the velocity set point is reduced to zero. Velocity-torque profile 500 is further implemented using hysteresis such that the velocity set point of the actuator is not increased back to velocities $v_3$, $v_2$, and $v_1$ until the torque of the actuator drops below torques $\tau_6$, $\tau_4$, and $\tau_2$, respectively. Where torques $\tau_6$, $\tau_4$, and $\tau_2$, are set below torques $\tau_5$, $\tau_3$, and $\tau_1$, respectively As discussed above and further emphasized here, FIG. 5 is merely an example which should not unduly limit the scope of the claims. One of ordinary skill in the art would recognize many variations, alternatives, and modifications. In some embodiments, properties of the end effector and the actuator other than torque may be used in the velocity profile. In some examples, force applied by the actuator may be used instead of torque. In some embodiments, fewer and/or more than three steps may optionally be used in the velocity-torque profile. In some embodiments, velocity-torque profile 500 may optionally be implemented without hysteresis by setting $\tau_2$ equal to $\tau_1$, setting $\tau_4$ equal to $\tau_3$, and setting $\tau_6$ equal to $\tau_5$. In some embodiments, a smooth velocity-torque profile, with or without hysteresis, may optionally be used instead of the step profile of FIG. 5. In some examples, the velocity-torque profile may optionally be linear, include a series of s-shaped smooth steps, and/or other monotonic profile where the velocity set point is computed as a function of the torque. In some embodiments, the torques used to determine the velocity set point may optionally be average torques, low-pass filtered torques, and/or the like.

Figure 6:
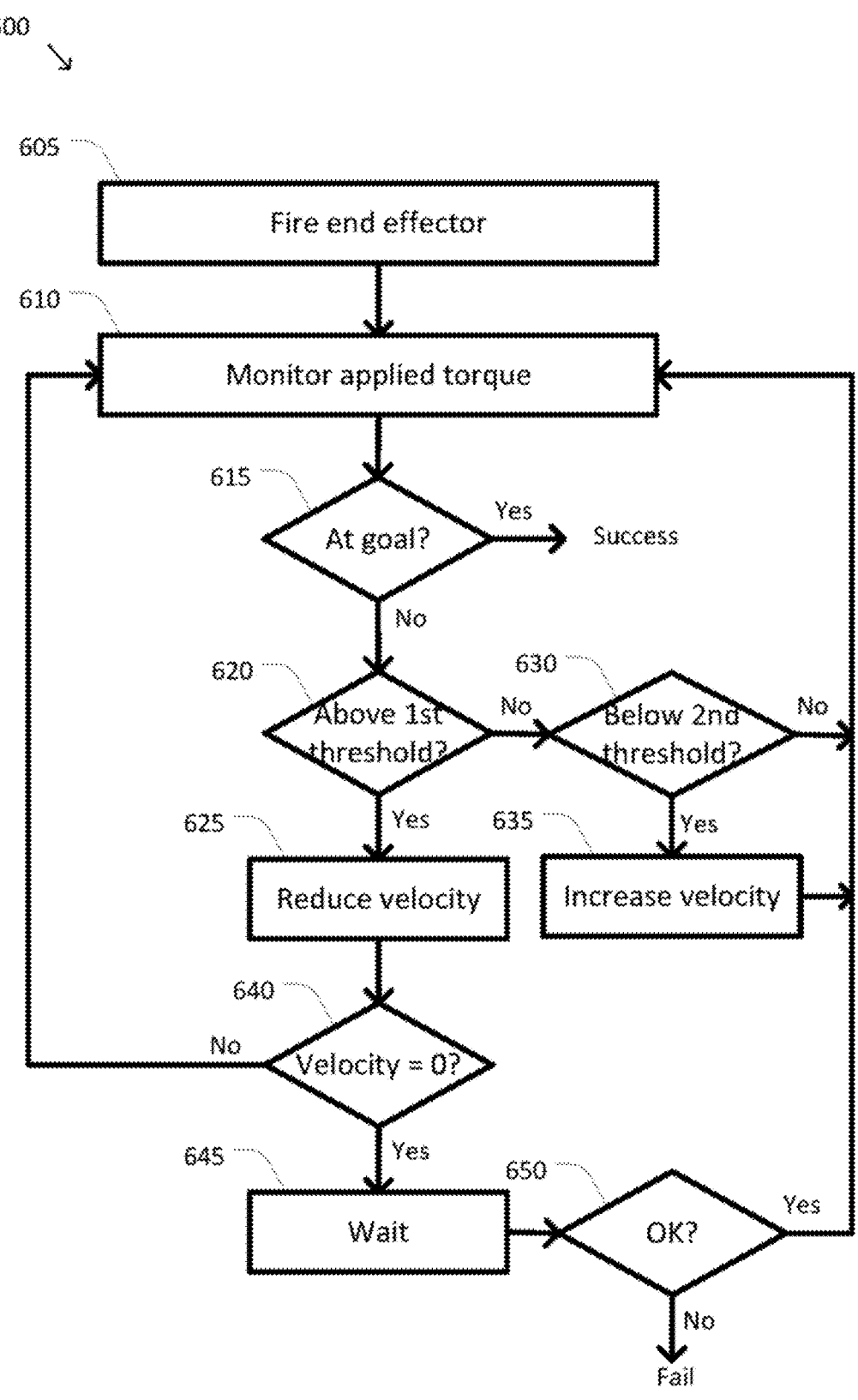
FIG. 6 is a simplified diagram of a method for performing a stapling and cutting operation according to some embodiments.

FIG. 6 is a simplified diagram of a method 600 for performing a stapling and cutting operation according to some embodiments. One or more of the processes 605-650 of method 600 may be implemented, at least in part, in the form of executable code stored on non-transient, tangible, machine readable media. This executable code, when run by one or more processors (e.g., the processor 150 in control unit 140), may cause the one or more processors to perform one or more of the processes 605-650. In some embodiments, method 600 may be performed by an application, such as control application 170. In some embodiments, method 600 may be used to limit the velocity of an actuator used to actuate a reciprocating element, such as reciprocating element 380, based on a torque being applied by the actuator. In some embodiments, the stapling and cutting operation of method 600 may be performed according to state machine 400 and/or velocity-torque profile 500. In some embodiments, the tests of processes 615, 620, and 630 may occur concurrently and/or in any order.

At a process 605, an end effector is actuated (also "fired"). The end effector, such as end effector 220, is fired by causing an actuator, such as an actuator in drive system 240, to apply a torque that is used to control at least one DOF of the end effector. In some examples, the actuator is controlled by sending one or more signals, such as a current, a voltage, a pulse-width modulated signal, and/or the like to the actuator. The actual effects of the firing of the end effector depend on the design, use, and purpose of the end effector. In some examples, firing of the end effector begins by setting a velocity set point of the actuator, such as the setting of the velocity set point to velocity $v_0$ during pre-clamp state 420. Using the examples, of FIGS. 2 and 3A-3D, the actuator applies a force to drive mechanism 250 which causes reciprocating element 380 to be moved toward the distal end of end effector 220. This in turn causes a reduction in the gap between anvil 360 and jaw 310 so that tissue is clamped, staples 330 are forced through the clamped tissue by sled 382 acting on staple pushers 335, and cutting blade 386 cuts the clamped tissue. The firing of the end effector continues until success or failure of the firing is determined and/or it is interrupted by an operator.

At a process 610, the applied torque is monitored. Using one or more sensors and/or control algorithms the torque being applied by the actuator is monitored as the end effector is fired. For example, when the actuator is a motor, current applied to the motor may be monitored and used to determine a torque being applied by the motor.

At a process 615, it is determined whether the end effector is at a goal position. Using one or more sensors, a position of the actuator and/or a position of a detectable location on the end effector is monitored. In some examples, the sensors may measure a rotation angle of a drive shaft of the actuator. In some examples, the one or more sensors may include a shaft encoder, Hall Effect sensor, and/or the like. In the examples, of FIGS. 3A-3D, the goal position corresponds to movement of reciprocating element 380 to the distal end of end effector 220 so that all of the staples 330 have been fired through the clamped tissue and cutting blade 386 has cut through the clamped tissue. When the goal position is reached, the operation of the end effector is considered successful and the velocity set point is set to zero. In some examples, an operator of the system is also notified via an audio and/or visual alert. In some examples, success is consistent with success state 480. When the goal position is not yet reached, the monitored torque is compared against one or more torque thresholds beginning with a process 620.

At the process 620, it is determined whether the applied torque is above a first torque threshold. The applied torque monitored during process 610 is compared to the first torque threshold to determine whether the actuator is applying more torque to the end effector than is desired. In some examples, the first torque threshold optionally varies depending upon the current velocity set point. In the examples, of FIGS. 4 and 5, the first torque threshold corresponds to one or more of the torques $\tau_1$, $\tau_3$, and/or $\tau_5$. When the applied torque is above the first torque threshold, the velocity set point is reduced using a process 625. When the applied torque is not above the first threshold, the torque is compared to a second torque threshold using a process 630.

At the process 625, the velocity set point is reduced. When the applied torque is above the first threshold, the velocity set point of the actuator is reduced to allow additional time for the clamped tissue to further desiccate, slow down the firing of one or more staples, and/or the like. In some examples, the velocity set point may be reduced a fixed amount, a percentage amount, according to a velocity-torque profile, and/or the like. In the examples of FIGS. 4 and 5, the velocity set point is reduced to $v_2$, $v_3$, or zero depending upon the previous velocity set point and/or the first torque threshold used during process 620. In some examples, the decreasing of the velocity set point is consistent with the state transitions from initial clamp state 430 to the first slow clamp state 440, from the first slow clamp state 440 to second slow clamp state 450, and/or from the second slow clamp state 450 to wait state 460. After the velocity set point is reduced, it is tested to determine whether it is reduced to zero using a process 640.

At the process 630, it is determined whether the applied torque is below a second threshold. The applied torque monitored during process 610 is compared to the second torque threshold to determine whether the actuator may be sped up. In some examples, the second torque threshold is set lower than the first torque threshold in order to provide hysteresis in the velocity set point. In some examples, the second torque threshold optionally varies depending upon the current velocity set point. In the examples, of FIGS. 4 and 5, the second torque threshold corresponds to one or more of the torques $\tau_2$, $\tau_4$, and/or $\tau_6$. When the applied torque is below the second torque threshold, the velocity set point is increased using a process 635. When the applied torque is not below the second threshold, the torque is monitored again using process 610.

At the process 635, the velocity set point is increased. When the applied torque is below the second threshold, the velocity set point of the actuator is increased to allow faster operation of the end effector. In some examples, the velocity set point may be increased a fixed amount (e.g., 0.1 to 2 mm/sec), a percentage amount (e.g., 5-25 percent), according to a velocity-torque profile, and/or the like. In some examples, when the velocity is at a maximum set point, the velocity set point is not further increased during process 635. In the examples of FIGS. 4 and 5, the velocity set point is increased to $v_1$, $v_2$, or $v_3$ depending upon the previous velocity set point and/or the second torque threshold used during process 630. In some examples, the increasing of the velocity set point is consistent with the state transitions from try state 470 to second slow clamp state 450, from second slow clamp state 450 to the first slow clamp state 440, and/or from the first slow clamp state 440 to initial clamp state 430. After the velocity set point is increased, the torque is monitored again using process 610.

At the process 640, it is determined whether the velocity set point is zero. When the velocity set point reaches zero, a delay is introduced using a process 645. When the velocity set point is not yet at zero, the torque is monitored again using process 610.

At the process 645, a wait (also "pause") occurs. When the velocity set point reaches zero, firing of the end effector is delayed for a predetermined period of time (e.g., 1-10 sec). In some examples, the predetermined period of time is tracked using a hardware and/or software timer. In the examples of FIG. 4, process 645 corresponds to wait state 460. After the delay times out, operation of the end effector is tested using a process 650.

At the process 650, it is determined whether operation of the end effector can continue. The velocity set point is set to a non-zero value, such as the velocity set point value before the last time process 625 was performed, and the torque applied by the actuator is monitored. In the examples, of FIG. 4, process 650 corresponds to try state 470. When the torque applied by the actuator continues to be above a maximum torque threshold, such as the first torque threshold used the last time process 620 was performed, the firing of the end effector is considered failed and the velocity set point is set to zero. In some examples, the firing of the end effector may optionally be reversed and/or one or more audio and/or visual alerts are optionally provided to an operator. When movement at the non-zero velocity set point occurs without an excessive applied torque being detected, the velocity set point is retained and the monitoring of the torque continues with process 610.

As discussed above and further emphasized here, FIG. 6 is merely an example which should not unduly limit the scope of the claims. One of ordinary skill in the art would recognize many variations, alternatives, and modifications. In some embodiments, properties of the end effector and the actuator other than torque may be monitored during process 610 and tested during processes 620 and 630. In some embodiments, the wait or process 645 and/or the test of process 650 may be repeated one, two, or more times before failure is concluded. In this way, the method 600 may pause the actuator multiple times and indicate a failure after a predetermined number of actuator pauses have occurred. In some examples, the number of repetitions may be tracked using a hardware or software counter.

In some embodiments, one or more techniques may optionally be used to reduce the effects of temporary transients in the application of the torque thresholds. In some examples, the comparisons of the applied torque to the first and second torque thresholds in processes 620 and 630, respectively, determine whether the applied torque remains above or below the first and second torque thresholds for a predetermined period of time. In some examples, the predetermined period of time may optionally be different for the first and second torque thresholds. In some examples, the monitoring of the applied torque in process 610 includes averaging the applied torque. In some examples, the averaging includes using exponential smoothing. In some examples, the monitoring of the applied torque in process 610 includes low-pass filtering the applied torque. These variations can also be applied to the other methods and states described by this disclosure.

Figure 7:
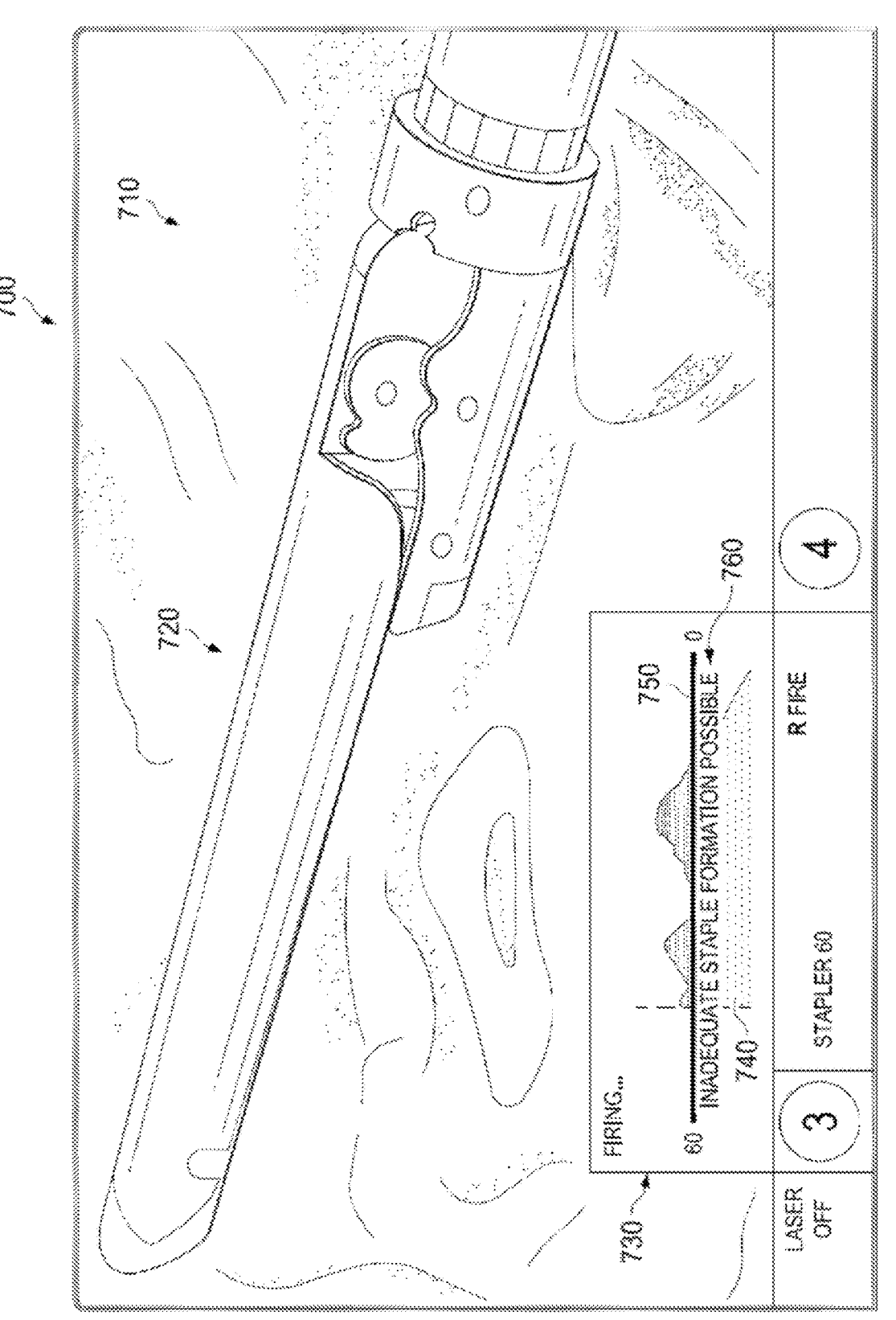
FIG. 7 shows a portion of an exemplary graphical user interface providing visual feedback regarding a stapling operation according to some embodiments.

FIG. 7 shows a portion of an exemplary graphical user interface (GUI) 700 providing visual feedback regarding a stapling operation according to some embodiments. GUI 700 may be shown on an electronic display of a computer-assisted system (e.g., computer-assisted system 100) or a display in communication with the computer-assisted system. In some embodiments, the control unit (e.g., control unit 140), comprises a display controller communicatively coupled with a processor of the control unit. The display controller is configured to operate the electronic display, and the processor is configured to provide images indicative of applied force or torque and/or fire progress or position to the display controller. This causes the display controller to provide visual feedback indicative of the applied force or torque and/or first progress or position using the electronic display. In some embodiments, the display controller is external to the control unit 140 and is communicatively coupled with the control unit 140 such that it can still receive images from the control unit 140 for display on the electronic display.

A medical stapler instrument 720, such as a stapler for applying 60 mm of staples, is shown in the middle of performing a stapling operation on a portion of patient tissue 710. GUI 700 includes a firing status region 730 that updates as the stapling operation proceeds. Firing status region 730 indicates a relative location of the staple firing mechanism (e.g., reciprocating element 380 and/or sled 382) using a firing profile 740, which reports the force and/or torque applied to the stapling mechanism as it moves from a right-most or proximal position ("0") to a left-most or distal position ("60"). Firing profile 740 further includes a threshold line 750 indicating a force or torque threshold that indicates when the applied force or torque the force or torque threshold that inadequate staple formation is likely to occur. In some examples, firing profile 740 may be rendered using colors and/or highlights that illustrate the likelihood of staple malformation. In some examples, regions of firing profile 740 below threshold line 750 may be rendered in green indicating a low or very low likelihood of staple malformation, the regions of firing profile just above threshold line 750 may be rendered using a color gradient from yellow closest to threshold line 750 to red the farther above threshold line 750 that firing profile 740 is rendered.

Firing status region 730 further indicates the type of instrument ("Stapler 60"), the control that can be used to fire the stapler instrument (the control associated with "R Fire"), and the stapling operation state ("Firing . . . "). In some examples, firing status region 730 may further include textual feedback 760 indicating, in textual form, an estimated likelihood of successful stapling (e.g., "inadequate staple formation possible"). This type of feedback can be used by the operator of the stapler instrument to better control the stapler operation, such as in making decisions on whether to proceed through the various stapler states such as the gripping, clamping-not-yet-firing, and firing states discussed in conjunction with FIG. 3A.

Figure 8:
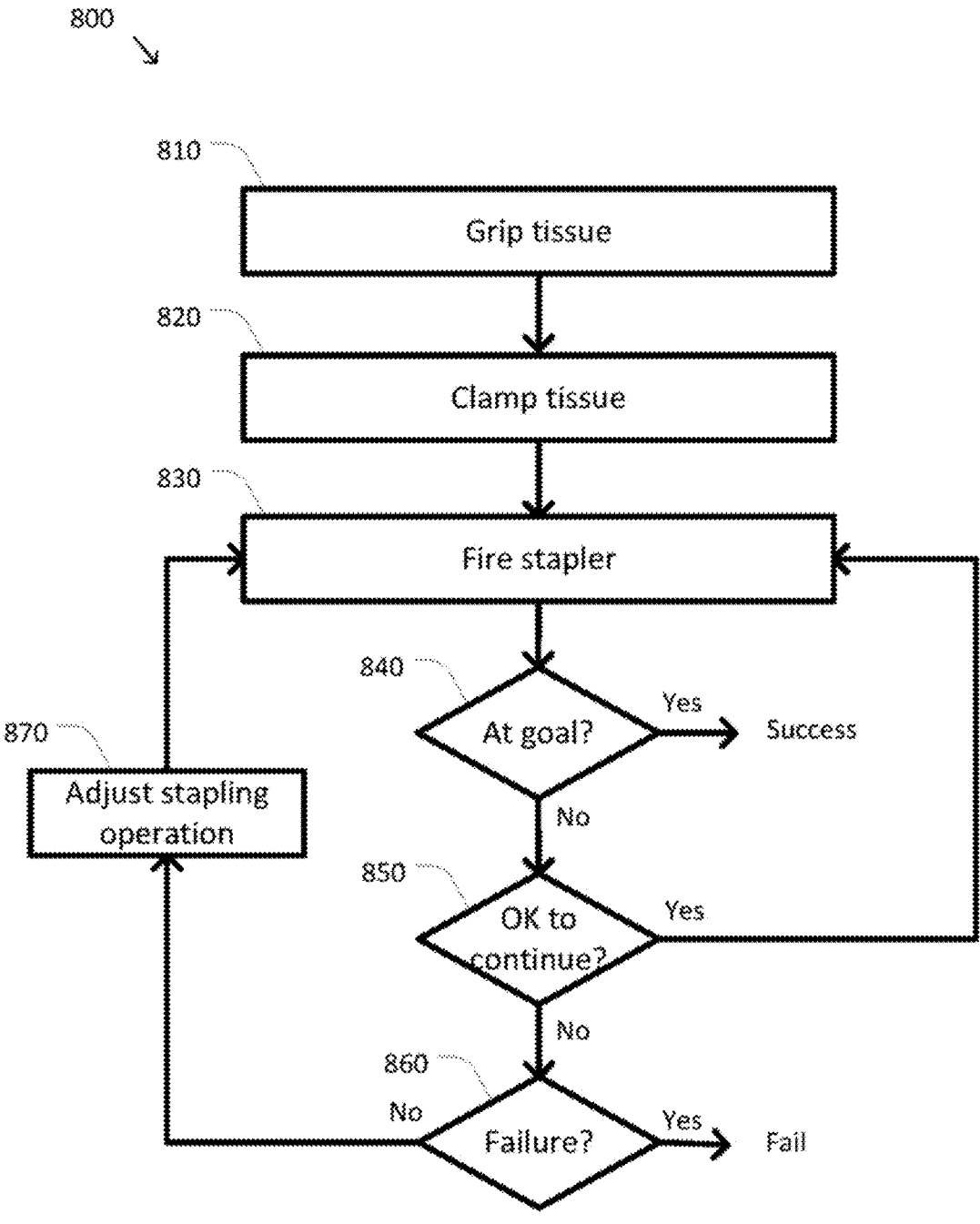
FIG. 8 is a simplified diagram of a method for performing a stapling operation according to some embodiments.

FIG. 8 is a simplified diagram of a method 800 for performing a stapling operation according to some embodiments. One or more of the processes 810-870 of method 800 may be implemented, at least in part, in the form of executable code stored on non-transient, tangible, machine readable media. This executable code, when run by one or more processors (e.g., the processor 150 in control unit 140), may cause the one or more processors to perform one or more of the processes 810-870. In some embodiments, method 800 may be performed by an application, such as control application 170. In some embodiments, method 800 may be used to control an actuator used to actuate a reciprocating element, such as reciprocating element 380, of a stapler based on active monitoring of the actuator. In some embodiments, one or more of the processes of method 800 may be performed concurrently. In some examples, the firing of process 830 may occur continuously while processes 840-860 are performed.

At a process 810, tissue is gripped. In some examples, the actuator is advanced so as apply a gripping force to the tissue using jaws of an end effector, such as end effector 220. In some examples, the actuator is controlled by sending one or more signals, such as a current, a voltage, a pulse-width modulated signal, and/or the like to the actuator. In some examples, process 810 may be similar to the process used for the gripping state described in conjunction with FIG. 3A where sled 382 is between dotted lines 392 and 394.

At a process 820, the tissue is clamped. Similar to process 810, the actuator is further advanced so as to apply a clamping force to the tissue using the jaws of the end effector. In some examples, the actuator is controlled by sending one or more signals, such as a current, a voltage, a pulse-width modulated signal, and/or the like to the actuator. In some examples, process 820 may be similar to the process used for the clamping-not-yet-firing state described in conjunction with FIG. 3A where sled 382 has reached dotted line 394. In some examples, transition from process 810 to 820 may further depend on receiving input from an operator, such as by activation of a clamping control, which may be implemented using a button, switch, lever, pedal, and/or the like.

At a process 830, the stapler is fired. Similar to processes 810 and/or 820, the actuator is further advanced so as to begin the stapling of the tissue. In some examples, process 830 may be similar to the process used for the firing state described in conjunction with FIG. 3A where sled 382 has advanced to dotted line 396 and beyond. In some examples, transition from process 820 to 830 may further depend on receiving input from an operator, such as by activation of a firing control, which may be implemented using a button, switch, lever, pedal, and/or the like. In some examples, the firing control may be the same or different from the clamping control.

In some examples, the control unit uses a non-zero velocity set point to control movement of the actuator during the staple firing of process 830. In some examples, the control unit further uses a force or torque limit set for the stapling operation and/or the stapling end effector. In some examples, the force or torque limit may correspond to the threshold associated with threshold line 750 that indicates the upper limit on applied force or torque below which proper staple formation is most likely to occur. In some examples, the velocity set point and/or the force or torque limit may correspond to any of the thresholds described in velocity profile 500. In some examples, process 830 may be similar to process 605.

At a process 840, it is determined whether the actuator or stapling mechanism, such as reciprocating element 380 and/or sled 382, is at a goal position. Using one or more sensors, a position of the actuator and/or a position of a detectable location on the stapling mechanism is monitored. In some examples, the sensors may measure a rotation angle of a drive shaft of the actuator. In some examples, the one or more sensors may include a shaft encoder, Hall Effect sensor, and/or the like. In the examples, of FIGS. 3A-3D, the goal position corresponds to movement of reciprocating element 380 to the distal end of end effector 220 so that sled 382 reaches dotted line 398 and all of the staples 330 have been fired through the clamped tissue and cutting blade 386 has cut through the clamped tissue. When the goal position is reached, the stapling is considered successful and the velocity set point is set to zero. In some examples, an operator of the system is also notified via an audio and/or visual alert. In some examples, success is consistent with success state 480. When the goal position is not yet reached, the operation of the stapler is further monitored to determine whether stapling may continue to proceed using a process 850.

At the process 850, it is determined whether stapling may continue. In some examples, the control unit determines whether the applied force or torque being applied by the actuator satisfies a continue condition. In some examples, the continue condition may correspond to the applied force or torque being equal to or lower than the force or torque limit used by the firing of process 830. When the continue condition is satisfied, then method 800 returns to process 830 where firing of the stapler continues. When the continue condition is not satisfied, then method 800 proceeds to a process 860 to determine whether stapling failure has occurred.

At the process 860, it is determined whether stapling failure has occurred. In some examples, the control unit determines whether the stapling operation satisfies one or more stapling failure conditions. In some examples, one of the stapling failure conditions may correspond to an inability to further advance the actuator when a maximum force or torque for the stapler is being applied by the actuator. In some examples, the inability to further advance may correspond to less than a threshold amount of further actuator advancement for a predetermined period of time.

In some examples, one of the stapling failure conditions may correspond to an aggregate measure of stapler pausing during the stapling of method 800. In some examples, the aggregate measure may correspond to a count of a number of pauses during a stapling operation exceeding a maximum number of pauses, such as 5 or 6, which may be set based on a type of stapler, a type of tissue being stapled, a type of procedure being performed, and/or the like. In some examples, the count may be maintained by incrementing a counter every time a pause occurs in the stapling operation. In some examples, the aggregate measure may correspond to a total duration of all pauses during the stapling operation exceeding a maximum duration, such as 40 seconds, which may be set based on a type of stapler, a type of tissue being stapled, a type of procedure being performed, and/or the like. In some examples, the total duration may be kept by starting a timer with the beginning of each pause in the stapling and stopping the timer at the end of each pause in the stapling operation. In some examples, the aggregate measure may correspond to the combination of both the count of the number of pauses exceeding the maximum number of pauses and the total duration of all the pauses exceeding the maximum duration.

When none of the stapling failure conditions is met, stapling continues by adjusting the stapling operation using a process 870. When the one or more stapling failure conditions are met, the firing of the stapler is considered failed and the velocity set point is set to zero. In some examples, the firing of the stapler may optionally be reversed and/or one or more audio and/or visual alerts are optionally provided to an operator.

At the process 870, an adjustment is made to the stapling operation. In some examples, the control unit adjusts one or more aspects of the stapling operation. In some examples, the control unit adjusts the stapling operation by adjusting the velocity set point of the actuator (e.g., by lowering it consistent with velocity profile 500 and/or process 625). Once the velocity set point is lowered, the firing of the stapler using process 830 occurs at the lowered velocity set point. In some examples, the control unit adjusts the stapling operation by setting the velocity set point to zero and causing the stapling operation to pause for a predetermined period of time. After the pause, the velocity may be returned to or set lower than the velocity set point used for firing before entering process 870. In some examples, each time process 870 pauses the stapling operation, the pause counter may be incremented and/or the total duration timer may be started. After process 870 adjusts the stapling operation, firing of the stapler continues by returning to process 830.

As discussed above and further emphasized here, FIG. 8 is merely an example which should not unduly limit the scope of the claims. One of ordinary skill in the art would recognize many variations, alternatives, and modifications. In some embodiments, method 800 may include additional processes to increase the velocity set point of the actuator in response to the applied force or torque being below a second threshold, where the second threshold is lower than a threshold used for the continue condition of process 850. In some examples, these additional processes may be consistent with processes 630 and/or 635.

Figure 9:
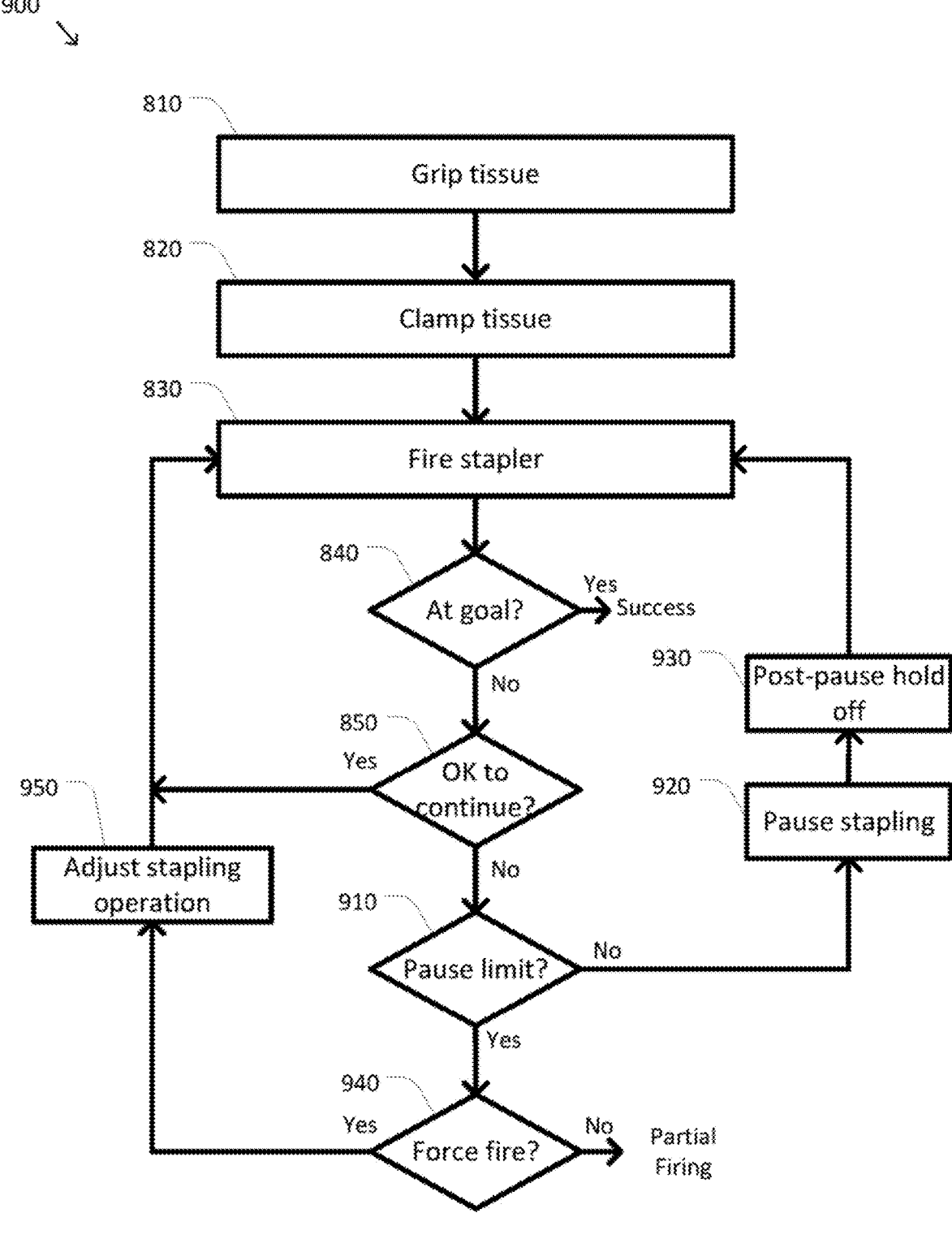
FIG. 9 is a simplified diagram of a method for performing a stapling operation according to some embodiments.

FIG. 9 is a simplified diagram of a method 900 for performing a stapling operation according to some embodiments. One or more of the processes 810-850 and 910-950 of method 900 may be implemented, at least in part, in the form of executable code stored on non-transient, tangible, machine readable media. This executable code, when run by one or more processors (e.g., the processor 150 in control unit 140), may cause the one or more processors to perform one or more of the processes 810-850 and 910-950. In some embodiments, method 900 may be performed by an application, such as control application 170. In some embodiments, method 900 may be used to control an actuator used to actuate a reciprocating element, such as reciprocating element 380 and/or sled 382, of a stapler based on active monitoring of the actuator. In some embodiments, one or more of the processes of method 900 may be performed concurrently. In some examples, the firing of 830 may occur continuously while processes 840, 850, 910-930, and/or 950 are performed.

Processes 810-850 of method 900 are substantially the same as processes 810-850 of method 800 with the exception that when the continue condition is not satisfied during process 850, then method 900 proceeds to a process 910 to determine whether a pause limit is reached.

At the process 910, it is determined whether a pause limit is reached. In some examples, the pause limit may correspond to an aggregate measure of stapler pausing during the stapling of method 900. In some examples, the aggregate measure may correspond to a count of a number of pauses (e.g., a number of times process 920 is performed as is discussed further below) during a stapling operation exceeding a maximum number of pauses, such as 5 or 6, which may be set based on a type of stapler, a type of tissue being stapled, a type of procedure being performed, and/or the like. In some examples, the count may be maintained using a pause counter.

In some examples, the aggregate measure may correspond to a total duration of all pauses during the stapling operation (e.g., an amount of time spent in process 920 as is discussed further below) exceeding a maximum duration, such as 40 seconds, which may be set based on a type of stapler, a type of tissue being stapled, a type of procedure being performed, and/or the like. In some examples, the total duration may be kept using a pause timer.

In some examples, the aggregate measure may correspond to the combination of both the count of the number of pauses exceeding the maximum number of pauses and the total duration of all the pauses exceeding the maximum duration. When the pause limit is not yet reached, the stapling is paused using a process 920. When the pause limit is reached, a determination is made as to whether forced firing of the stapler should occur using a process 940.

At the process 920, stapling is paused. In some examples, the control unit saves the current velocity set point for the stapler and pauses the stapling by reducing the velocity set point and/or setting the velocity set point to zero and causing the actuator used to actuate the reciprocating element, such as reciprocating element 380 and/or sled 382, of the stapler to stop moving. In some examples, even though the actuator is paused, the actuator may continue to apply force to the clamped tissue, which may cause additional tissue desiccation and/or compression. This additional tissue desiccation and/or compression may permit further stapling to occur without the applied force or torque of the stapler exceeding the force or torque limit described during process 850.

In some examples, the pause of process 920 may continue for a predetermined duration. In some examples, the predetermined duration may be implemented using a duration timer, which is started when process 920 is entered and causes process 920 to exit when the duration timer reaches the predetermined duration. In some examples, the pause of process 920 may alternatively be ended early when the applied force or torque of the actuator falls below a force or torque threshold that is lower than the force or torque limit used during process 850. In some examples, the force or torque threshold of process 920 may be set to a percentage of (e.g., 40-80 percent) and/or a predetermined offset below (e.g., 100 to 350 N) of the force or torque limit of process

850. In some examples, the reduction in the applied force or torque may indicate sufficient tissue desiccation and/or compression to continue the stapling operation.

The pausing of process 920 is further monitored to support the pause limit determination of process 910. In some examples, each time process 920 is performed, the pause counter is incremented. In some examples, each time process 920 initiates a pause, the pause timer is started to continue to track the total duration of all the pauses and the pause timer is stopped when the pause ends, either by expiration of the duration timer and/or early termination of the pause due to the applied force or torque dropping below the force or torque threshold. After the pause ends, a post-pause hold off period begins using a process 930.

At the process 930, a post-pause hold off period is initiated. During the post-pause hold off period, firing of the stapler is resumed by resetting the velocity set point for the stapler to the velocity set point saved during process 920 or to another velocity set point. The control unit prevents process 910 from triggering an additional pause using process 920 until after the post-pause period expires. In some examples, the post-pause hold off period is enforced for a predetermined period of time (e.g., 0.5-1.5 sec) using, for example, a timer and/or until the stapling has successfully proceeded for a predetermined distance (e.g., 0.5-3 mm). In some examples, post-pause hold off period may by consistent with and/or similar to try state 470. After the post-pause hold off period ends, firing of the stapler using process 830 continues using the loop of processes 830-850 and 910-930.

When process 910 detects that a pause limit is exceeded, the process 940 determines whether forced firing of the stapler should occur. In some examples, forced firing corresponds to operating the stapler in a mode where the applied force or torque is allowed to exceed the upper limit on applied force or torque (e.g., the force or torque corresponding to threshold line 750) above which inadequate staple formation is possible and/or likely to occur. In some examples, during process 940, the operator of the stapler is notified that the stapler is stalled (e.g., because a pause limit has been reached) using an audio and/or visual alert, such as by utilizing textual feedback 760. Once the operator is notified of the stall, process 940 waits for initiation of forced firing by the operator using a forced firing control. In some examples, the forced firing control may be implemented using a button, switch, lever, pedal, and/or the like. In some examples, the forced firing control may be different from the clamping control. In some examples, firing of the stapler while in process 940 may be paused, such as by saving the current velocity set point and setting the velocity set point to zero. In some examples, when forced firing of the stapler is initiated using process 940, the success notification after process 840 determines that the goal position is reached may be modified to indicate that inadequate staple formation is possible and/or likely. When forced firing is not initiated, the stapling operation is terminated and the operator is notified using an audio and/or visual alert (e.g., utilizing textual feedback 760) that partial stapling has occurred and that one or more staples may not have been fired through the tissue. In some examples, the firing of the stapler may optionally be reversed upon the determination of partial firing. When forced firing is initiated, the stapling operation is adjusted using process 950.

At the process 950, the stapling operation is adjusted to allow for forced firing of the stapler. In some examples, the control unit adjusts the stapling operation by increasing the force or torque limit for the stapler to a level that does not exceed the maximum force or torque limit for the stapler. In some examples, the force or torque limit is increased to the maximum force or torque limit for the stapler. In some examples, the force or torque limit is increased to a value between the previous force or torque limit and the maximum force or torque limit. In some examples, the force or torque limit may be increased by a percentage of the maximum force or torque (e.g., 10-100 percent) and/or by a fixed amount (e.g., 150 to 600 N). Once the force or torque limit is increased, the velocity set point is reset (e.g., to the velocity set point saved during process 940). In some examples, one or more other parameters of the stapling operation may alternatively and/or additionally adjusted. In some examples, the one or more other parameters may include the velocity set point, the pause limit (e.g., max number of pauses or max duration), and/or the like. After the stapling operation is adjusted, firing of the stapler continues by returning to process 830.

As discussed above and further emphasized here, FIG. 9 is merely an example which should not unduly limit the scope of the claims. One of ordinary skill in the art would recognize many variations, alternatives, and modifications. In some embodiments, processes 910 and/or 920 may implement multiple maximum numbers of pauses and/or multiple maximum durations. In some examples, the multiple maximum numbers of pauses and/or multiple maximum durations may include both "local" and "global" maximum numbers of pauses and/or "local" and "global" maximum durations. In some examples, the local number of pauses and/or local maximum duration may apply to a relatively shorter span, such as a few millimeters for a 60 millimeter stapler, of stapler actuation such that when stapling progress longer than the shorter span is achieved, with or without a pause, the local number of pauses and/or local maximum duration are reset. In some examples, the global number of pauses and/or global maximum duration may apply to a longer span and/or to the entire span of the stapler actuation. In some examples, the multiple maximum numbers of pauses and/or multiple maximum durations may include a maximum number of pauses and/or a maximum duration for three, four, or more spans of various lengths. In some examples, exceeding any of the maximum numbers of pauses and/or any of the maximum durations during process 910 may cause method 900 to move to process 940 to determine whether forced firing of the stapler should occur.

In some embodiments, the number of times the determination of whether forced firing should occur using process 940 may be limited. In some examples, process 940 may be skipped and the notification of partial firing may be indicated when the pause limit is reached and the force or torque limit for the stapler is already set to the maximum force or torque limit for the stapler. In some examples, process 940 may be performed up to a predetermined number of times, such as once, twice, three times, or more so as to limit the number of forced firing cycles and/or the reduce the likelihood of damage to the stapler and/or undesired injury to the tissue being stapled.

Figure 10:
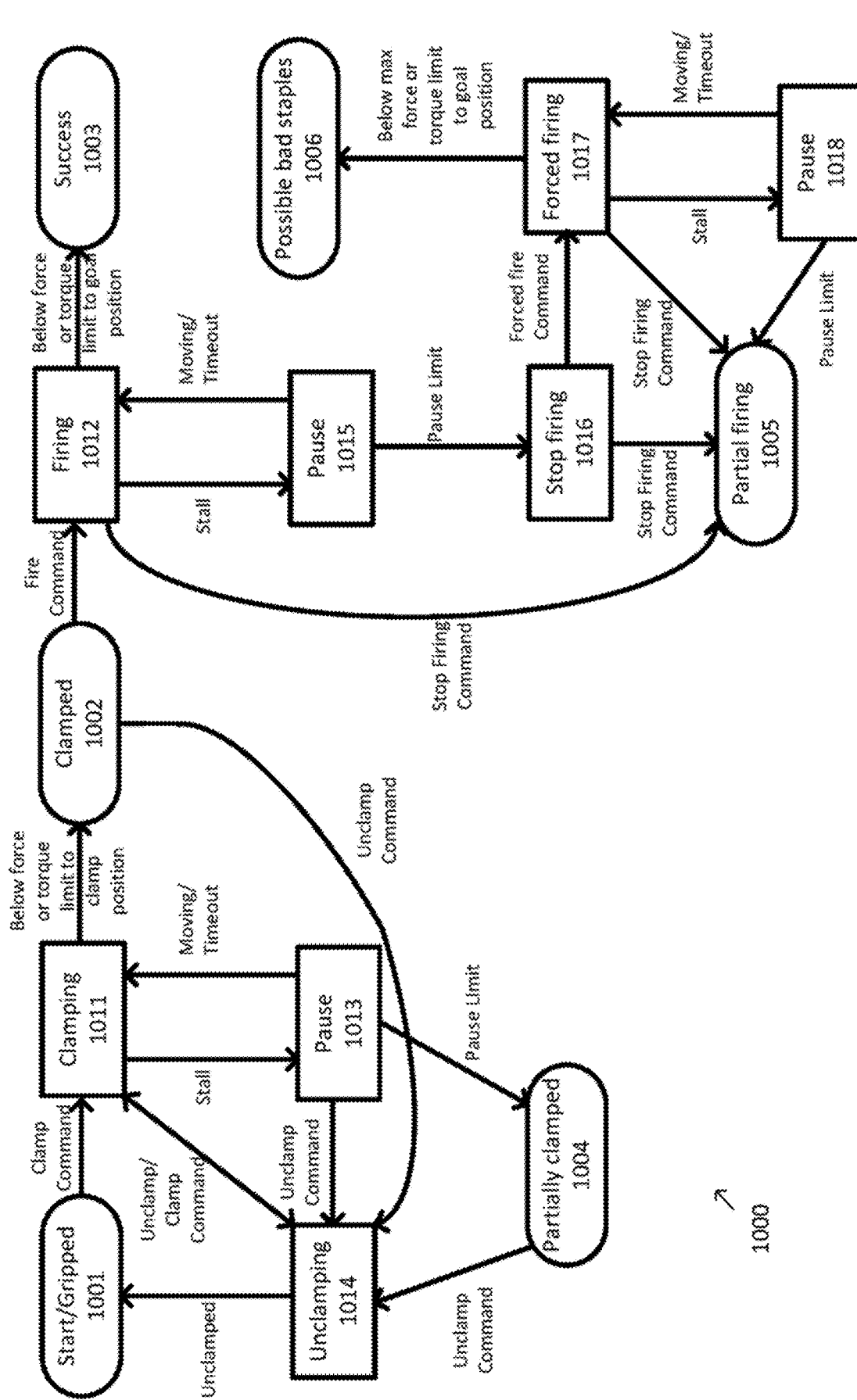
FIG. 10 is a simplified diagram of an operational state machine illustrating an approach to performing a stapling operation according to some embodiments.

FIG. 10 is a simplified diagram of an operational state machine 1000 illustrating an approach to performing a stapling operation according to some embodiments. One or more of the states 1001-1018 of state machine 1000 may be implemented, at least in part, in the form of executable code stored on non-transient, tangible, machine readable media. This executable code, when run by one or more processors (e.g., the processor 150 in control unit 140), may cause the one or more processors to implement one or more of the states 1001-1018. In some embodiments, state machine 1000 may be implemented by an application, such as control application 170. In some embodiments, state machine 1000 may be used to control an actuator, such as the actuator controlling movement of reciprocating element 380 and/or sled 382, based on operator input and monitoring of a stapling operation.

State machine 1000 begins in a start or gripped state 1001, which may correspond to the gripping state described with respect to FIG. 3A. In the start or gripped state 1001, the tissue that is to be subject to the stapling operation has already been gripped by the jaws of the stapler, such as the jaws of end effector 220. Upon receiving a clamp command from an operator, such as a surgeon, via the activation of one or more controls, inputs, and/or the like, operation of the stapler transitions to a clamping state 1011.

While in clamping state 1011, the actuator of the stapler is further advanced in order to clamp the gripped tissue. In some examples, the clamping of clamping state 1011 is consistent with the clamping of tissue by process 820. While the stapler is attempting to clamp the tissue, the operator may stop the clamping by providing an unclamp command using one or more controls, inputs, and/or the like, which, in some examples, may be the same one or more controls, inputs, and/or the like used to provide the clamp command used to enter clamping state 1011. When the unclamp is received, state machine 1000 transitions to unclamping state 1014 as is described further below. While in clamping state 1011, the clamping by the stapler is monitored to determine whether the clamping operation has stalled, such as by detecting the lack of sufficient forward movement by the actuator over a predetermined period of time and/or an applied force or torque of the actuator exceeding a force or torque limit. When a stall is detected, state machine 1000 transitions to a pause state 1013 as is described further below. When the applied force or torque of the actuator remains below the force or torque limit and the clamp position is reached (e.g., the position corresponding to dotted line 394 of FIG. 3A), state machine 1000 transitions to clamped state 1002.

Clamped state 1002 corresponds to the tissue being successfully clamped by the jaws of the stapler and may correspond to the clamping-not-firing state described with respect to FIG. 3A. When an unclamp command is received in clamped state 1002 (e.g., by toggling and/or deactivating the same one or more controls, inputs, and/or the like used for the unclamp command while in clamping state 1011), state machine 1000 transitions to unclamping state 1014. When a fire command is received in clamped state 1002, state machine 1000 transitions to firing state 1012. The fire command may be received from the operator using one or more controls, inputs, and/or the like, which, in some examples, are different from the one or more controls, inputs, and/or the like used for the clamp and/or unclamp commands.

In firing state 1012, force or torque is applied to the actuator and stapling of the clamped tissue is attempted. While in firing state 1012, the control unit attempts to advance the actuator so as to fire one or more staples through the clamped tissue (e.g., by advancing sled 382 past dotted line 396 toward dotted line 398). In some examples, firing state 1012 may implemented consistent with the approach used by processes 605 and/or 830 in conjunction with methods 600, 800, and/or 900. While in firing state 1012, the firing of the stapler is monitored to determine whether the firing operation has stalled, such as by detecting the lack of sufficient forward movement by the actuator over a prede-termined period of time and/or an applied force or torque of the actuator exceeding a force or torque limit. When a stall is detected, state machine 1000 transitions to a pause state 1015 as is described further below. When a stop firing command is received while in firing state 1012, state machine 1000 transitions to partial firing state 1005. In some examples, the stop firing command may be received from the same one or more controls, inputs, and/or the like used to provide the fire command while in clamped state 1002 (e.g., by toggling and/or deactivating the one or more controls, inputs, and/or the like used to provide the fire command). When the applied force or torque of the actuator remains below the force or torque limit and the goal position is reached (e.g., the position corresponding to dotted line 398 of FIG. 3A), state machine 1000 transitions to a success state 1003.

In success state 1003, success of the stapling operation with proper staple formation is indicated to the operator, such as by sending a notification to the operator as is described with respect to processes 615 and/or 840. In some examples, the notification may include using textual feed-back 760.

In unclamping state 1014, force or torque is applied to the actuator so as to reverse operation of the jaws of the stapler and to reduce force on the partially clamped tissue. When the actuator has been sufficiently reversed so that the tissue is unclamped (e.g., to a position corresponding to dotted line 392), state machine 1000 returns to the start or gripped state 1001. While in unclamping state 1014, the unclamp com-mand may be replaced with a clamp command (e.g., by toggling and/or deactivating the one or more controls, inputs, and/or the like used to provide the unclamp com-mand) with state machine 1000 returning to clamping state 1011.

In pause state 1013, clamping of the tissue is paused with the tissue partially clamped. In some examples, the pause may be implemented by setting the velocity set point for the stapler to a small or zero velocity set point value using an approach similar to those discussed with respect to processes 870 and/or 920 that are used to implement a similar pause during firing. While in the pause state 1013, when the actuator beings to move again and is able to continue clamping (e.g., as the partially clamped tissue begins to desiccate or compress), state machine 1000 returns to clamp-ing state 1011. Alternatively, state machine 1000 may return to clamping state 1011 automatically after a predetermined time has elapsed. When an unclamp command is received while in pause state 1013, state machine 1000 transitions to unclamping state 1014. In some examples, the unclamp command may be received from the same one or more controls, inputs, and/or the like used to provide the unclamp command while in clamping state 1011. While in pause state 1013, when a pause limit is reached, state machine 1000 transitions to a partially clamped state 1004. In some examples, the pause limit may be consistent with the pause limits of processes 850 and/or 910 as applied to clamping rather than firing.

In partially clamped state 1004, further movement and clamping of the jaws of the stapler is stopped (e.g., by setting the velocity set point to zero) and the operator is notified using an audio and/or visual alert of the partial clamping condition. In some examples, the notification may include using textual feedback 760. When an unclamp command is received while in partially clamped state 1004, state machine 1000 transitions to unclamping state 1014. In some examples, the unclamp command may be received from the same one or more controls, inputs, and/or the like used to provide the unclamp command while in clamping state 1011.

In pause state 1015, firing of the stapler is paused while the stapler is only partially fired. In some examples, the pause may be implemented by setting the velocity set point for the stapler to a small or zero velocity set point value using the approach of processes 870 and/or 920. While in pause state 1015, when the actuator beings to move again and is able to continue firing (e.g., as the clamped tissue begins to further desiccate or compress), state machine 1000 returns to firing state 1012. Alternatively, state machine 1000 may return to firing state 1012 automatically after a predetermined time has elapsed. While in pause state 1015, when a pause limit is reached, state machine 1000 transitions to a stop firing state 1016. In some examples, the pause limit may be consistent with the pause limits of processes 850 and/or 910.

In stop firing state 1016, firing of the stapler is stopped (e.g., by setting the velocity set point to zero) and the operator is notified using an audio and/or visual alert of the partial firing condition. In some examples, stop firing state 1016 may be implemented using process 940. In some examples, the notification may include using textual feedback 760. In some examples, the notification may further include a prompt asking the operator whether forced firing is desired. When a stop firing command is received while in stop firing state 1016, state machine 1000 transitions to partial firing state 1005. In some examples, the stop firing command may be received from the same one or more controls, inputs, and/or the like used to provide the stop firing command while in firing state 1012. When a forced fire command is received during stop firing state 1016, state machine transitions to forced firing state 1017. In some examples, this transition to forced firing state 1017 may correspond to method 900 transitioning from process 940 to process 950.

In partial firing state 1005, operation of the stapler is halted (e.g., by setting the velocity set point to zero) and the operator is notified using an audio and/or visual alert that not all the staples have been fired through the tissue. In some examples, the notification may include using textual feedback 760.

In forced firing state 1017, one or more parameters of the stapling operation are adjusted so that at the risk of possible inadequate staple formation, the stapling operation is allowed to proceed. In some examples, the one or more parameters may be altered using process 950. Once the one or more parameters are altered, firing of the stapler continues such as by continuing with process 830 using method 900. When the goal position (e.g., the position corresponding to dotted line 398) is reached and without the applied force or torque of the actuator having to exceed the maximum force or torque limit for the stapler, state machine 1000 transitions to a possible bad staples state 1006. While in forced firing state 1017, the firing of the stapler is monitored to determine whether the firing operation has stalled, such as by detecting the lack of sufficient forward movement by the actuator over a predetermined period of time and/or an applied force or torque of the actuator exceeding the force or torque limit altered to begin forced firing. When a stall is detected, state machine 1000 transitions to a pause state 1018 as is described further below. When a stop firing command is received while in forced firing state 1017, state machine 1000 transitions to partial firing state 1005. In some examples, the stop firing command may be received from the same one or more controls, inputs, and/or the like used to provide the stop fire command while in firing state 1012.

In the possible bad staples state 1006, the stapling operation is considered complete and the operator is notified using an audio and/or visual alert that the staling operation has completed, but that one or more inadequately formed staples may be present. In some examples, the notification may include using textual feedback 760.

In pause state 1018, firing of the stapler is paused while the stapler is only partially fired. In some examples, the pause may be implemented by setting the velocity set point for the stapler to a small or zero velocity set point value using the approach of processes 870 and/or 920. While in pause state 1018, when the actuator beings to move again and is able to continue firing (e.g., as the clamped tissue begins to further desiccate or compress), state machine 1000 returns to forced firing state 1017. Alternatively, state machine 1000 may return to forced firing state 1017 automatically after a predetermined time has elapsed. While in pause state 1018, when a pause limit is reached, state machine 1000 transitions to a partial firing state 1005. In some examples, the pause limit may be consistent with the pause limits of processes 850 and/or 910.

As discussed above and further emphasized here, FIG. 10 is merely an example which should not unduly limit the scope of the claims. One of ordinary skill in the art would recognize many variations, alternatives, and modifications. In some embodiments, state machine 1000 may include additional transitions. In some examples, each of success state 1003, partial firing state 1005, and/or possible bad staples 1006 may include a transition to unclamping state 1014 when an unclamp command is received.

Some examples of control units, such as control unit 140 may include non-transient, tangible, machine readable media that include executable code that when run by one or more processors (e.g., processor 150) may cause the one or more processors to implement the states of state machine 400, implement the velocity-torque profile 500, and/or perform the processes of method 600. Some common forms of machine readable media that may include the implementation of state machine 400, the implementation of velocity-torque profile 500, and/or the processes of method 600 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Some examples of control units, such as control unit 140 may include non-transient, tangible, machine readable media that include executable code that when run by one or more processors (e.g., processor 150) may cause the one or more processors to implement the states of state machine 400 and/or 1000, implement the velocity-torque profile 500, and/or perform the processes of methods 600, 800, and/or 900. Some common forms of machine readable media that may include the implementation of state machine 400 and/or 1000, the implementation of velocity-torque profile 500, and/or the processes of methods 600, 800, and/or 900 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
an actuator; and
one or more processors;
wherein to perform an operation with an instrument coupled to the actuator, the one or more processors are configured to operate the instrument according to a state machine by:
transitioning the instrument from a gripped state to a clamped state in response to receiving a clamp command;
transitioning the instrument from the clamped state to a firing state in response to receiving a fire command;
transitioning the instrument from the firing state to a pause state in response to detecting a stall in the actuator used to actuate the instrument;
transitioning the instrument from the pause state to a stop firing state in response to a pause limit being reached, the pause limit comprising a count of a number of pauses during operation of the instrument being above a predetermined number of pauses, a total duration of all pauses during the operation of the instrument being above a maximum pause duration, or the count of the number of pauses during the operation of the instrument being above the predetermined number of pauses and the total duration of all pauses during the operation of the instrument being above the maximum pause duration; and
transitioning the instrument from the pause state to the firing state in response to the actuator beginning to move again or after a first predetermined period of time has elapsed since entering the pause state.

2. The computer-assisted device of claim 1, wherein to detect the stall in the actuator, the one or more processors are configured to detect a lack of motion of the actuator over a second predetermined period of time, an amount of force being applied by the actuator exceeding a force threshold, or an amount of torque being applied by the actuator exceeding a torque threshold.

3. The computer-assisted device of claim 2, wherein transitioning the instrument from the gripped state to the clamped state comprises determining that a clamp position is reached while the amount of force applied by the actuator remains below the force threshold or the amount of torque applied by the actuator remains below the torque threshold.

4. The computer-assisted device of claim 1, wherein transitioning the instrument from the firing state to the pause state comprises setting a velocity set point of the actuator to a zero velocity.

5. The computer-assisted device of claim 1, wherein, in response to a reciprocating element of the instrument traveling a predetermined distance, the one or more processors are further configured to reset the count of the number of pauses or reset the total duration of all pauses.

6. The computer-assisted device of claim 1, wherein operating the instrument according to the state machine further comprises:
providing, while in the stop firing state, an alert to an operator.

7. The computer-assisted device of claim 1, wherein operating the instrument according to the state machine further comprises:
transitioning the instrument from the stop firing state to a forced firing state in response to receiving a forced firing command; and
increasing, while in the forced firing state, a force or torque limit of the instrument to a maximum force or torque limit for the instrument.

8. The computer-assisted device of claim 7, wherein operating the instrument according to the state machine further comprises:
transitioning the instrument from the forced firing state to a possible bad staples state in response to a reciprocating member of the instrument reaching a goal position without an amount of force or torque applied by the actuator exceeding the maximum force or torque limit; and
providing, while in the possible bad staples state, an alert to an operator that inadequate staple formation may have occurred.

9. The computer-assisted device of claim 7, wherein operating the instrument according to the state machine further comprises:
transitioning the instrument from the forced firing state to a second pause state in response to detecting another stall in the actuator while in the forced firing state.

10. The computer-assisted device of claim 1, wherein operating the instrument according to the state machine further comprises:
transitioning the instrument from the clamped state to an unclamping state in response to receiving an unclamp command.

11. The computer-assisted device of claim 10, wherein operating the instrument according to the state machine further comprises:
transitioning the instrument from the unclamping state to the clamped state in response to the unclamp command being replaced with the clamp command.

12. The computer-assisted device of claim 1, wherein operating the instrument according to the state machine further comprises:
transitioning the instrument from the pause state to the stop firing state in response to a second pause limit being reached, the second pause limit comprising a count of a number of pauses during operation of the instrument where the actuator attempts to move a reciprocating element of the instrument over a predetermined portion of a total distance the reciprocating element can travel being above a second predetermined number of pauses, a total duration of pauses during the operation of the instrument as the actuator attempts to move the reciprocating over the predetermined portion of the total distance being above a second maximum pause duration, or the count of the number of pauses during the operation of the instrument as the actuator attempts to move the reciprocating over the predetermined portion of the total distance being above the second predetermined number of pauses and the total duration of pauses during the operation of the instrument as the actuator attempts to move the reciprocating over the predetermined portion of the total distance being above the second maximum pause duration.

13. A method of operating an instrument for use with a computer-assisted device comprising one or more processors, the method comprising:

transitioning, by the one or more processors, an instrument coupled to the computer-assisted device from a gripped state to a clamped state in response to receiving a clamp command;

transitioning, by the one or more processors, the instrument from the clamped state to a firing state in response to receiving a fire command;

transitioning, by the one or more processors, the instrument from the firing state to a pause state in response to detecting a stall in an actuator used to actuate the instrument;

transitioning, by the one or more processors, the instrument from the pause state to a stop firing state in response to a pause limit being reached, the pause limit comprising a count of a number of pauses during operation of the instrument being above a predetermined number of pauses, a total duration of all pauses during the operation of the instrument being above a maximum pause duration, or the count of the number of pauses during the operation of the instrument being above the predetermined number of pauses and the total duration of all pauses during the operation of the instrument being above the maximum pause duration; and transitioning, by the one or more processors, the instrument from the pause state to the firing state in response to the instrument beginning to move again or after a first predetermined period of time has elapsed since entering the pause state.

14. The method of claim 13, wherein detecting the stall in the instrument comprises detecting a lack of motion of the actuator over a second predetermined period of time, an amount of force being applied by the actuator exceeding a force threshold, or an amount of torque being applied by the actuator exceeding a torque threshold.

15. The method of claim 13, further comprising:

in response to a reciprocating element of the instrument traveling a predetermined distance, resetting, by the one or more processors, the count of the number of pauses or reset the total duration of all pauses.

16. The method of claim 13, further comprising:

providing, by the one or more processors while in the stop firing state, an alert to an operator;

transitioning, by the one or more processors, the instrument from the stop firing state to a forced firing state in response to receiving a forced firing command; and increasing, while in the forced firing state, a force or torque limit of the instrument to a maximum force or torque limit for the instrument.

17. The method of claim 16, further comprising:

transitioning, by the one or more processors, the instrument from the forced firing state to a possible bad staples state in response to a reciprocating member of the instrument reaching a goal position without an amount of force or torque applied by the actuator exceeding the maximum force or torque limit; and providing, by the one or more processors while in the possible bad staples state, an alert to the operator that inadequate staple formation may have occurred.

18. The method of claim 13, further comprising:

transitioning, by the one or more processors, the instrument from the stop firing state to a forced firing state in response to receiving a forced firing command; and increasing, by the one or more processors while in the forced firing state, a force or torque limit of the instrument to a maximum force or torque limit for the instrument.

19. A non-transitory machine-readable medium comprising a plurality of machine-readable instructions which when executed by one or more processors associated with a computer-assisted device are adapted to cause the one or more processors to perform a method comprising:

transitioning an instrument coupled to the computer-assisted device from a gripped state to a clamped state in response to receiving a clamp command;

transitioning the instrument from the clamped state to a firing state in response to receiving a fire command;

transitioning the instrument from the firing state to a pause state in response to detecting a stall in an actuator used to actuate the instrument;

transitioning the instrument from the pause state to a stop firing state in response to a pause limit being reached, the pause limit comprising a count of a number of pauses during operation of the instrument being above a predetermined number of pauses, a total duration of all pauses during the operation of the instrument being above a maximum pause duration, or the count of the number of pauses during the operation of the instrument being above the predetermined number of pauses and the total duration of all pauses during the operation of the instrument being above the maximum pause duration; and transitioning the instrument from the pause state to the firing state in response to the instrument beginning to move again or after a first predetermined period of time has elapsed since entering the pause state.

20. The non-transitory machine-readable medium of claim 19, wherein detecting the stall in the instrument comprises detecting a lack of motion of the actuator over a second predetermined period of time, an amount of force being applied by the actuator exceeding a force threshold, or an amount of torque being applied by the actuator exceeding a torque threshold.

* * * * *